United States Patent
Daniels

(10) Patent No.: US 11,786,307 B2
(45) Date of Patent: Oct. 17, 2023

(54) VISUALIZATION AND MANIPULATION OF RESULTS FROM A DEVICE-TO-IMAGE REGISTRATION ALGORITHM

(71) Applicant: CANON U.S.A., INC., Melville, NY (US)

(72) Inventor: Barret Daniels, Cambridge, MA (US)

(73) Assignee: Canon U.S.A., Inc., Melville, NY (US)

(*) Notice: Subject to any disclaimer, the term of this patent is extended or adjusted under 35 U.S.C. 154(b) by 970 days.

(21) Appl. No.: 16/566,654

(22) Filed: Sep. 10, 2019

(65) Prior Publication Data

US 2020/0121392 A1    Apr. 23, 2020

Related U.S. Application Data

(60) Provisional application No. 62/747,913, filed on Oct. 19, 2018.

(51) Int. Cl.
*A61B 34/10* (2016.01)
*A61B 90/11* (2016.01)
(Continued)

(52) U.S. Cl.
CPC .............. *A61B 34/10* (2016.02); *A61B 18/02* (2013.01); *A61B 34/25* (2016.02); *A61B 90/11* (2016.02);
(Continued)

(58) Field of Classification Search
CPC .................................. A61B 34/10; A61B 90/11
See application file for complete search history.

(56) References Cited

U.S. PATENT DOCUMENTS

| 7,491,198 B2 | 2/2009 | Kockro |
| 7,885,441 B2 | 2/2011 | Node-Langlois et al. |

(Continued)

FOREIGN PATENT DOCUMENTS

| JP | 2007-512854 A | 5/2007 |
| JP | H04-076788 B2 | 4/2008 |

(Continued)

OTHER PUBLICATIONS

Shenyang Xu, et al., "Gradient Vector Flow: A New External Force for Snakes", IEEE Proc. Conf. on Comp. Vis. Patt. Recog. (CVPR'97), Los Alamitos: Comp. Soc. Press, Jul. 1997, pp. 66-71.

(Continued)

*Primary Examiner* — Angela M Hoffa
*Assistant Examiner* — Younhee Choi
(74) *Attorney, Agent, or Firm* — Canon U.S.A., Inc. I.P. Division

(57) ABSTRACT

One or more devices, systems, methods and storage mediums for performing medical procedure (e.g., needle guidance, ablation, biopsy, etc.) planning and/or performance, and/or for performing visualization and manipulation of registration result(s), are provided. Examples of applications for such devices, systems, methods and storage mediums include imaging, evaluating and diagnosing biological objects, such as, but not limited to, lesions and tumors, and such devices, systems, methods and storage mediums may be used for radiotherapy applications (e.g., to determine whether to place seed(s) for radiotherapy). The devices, systems, methods and storage mediums provided herein provide improved registration results by providing one or more of the following: automatic multi-planar reconstruction of a device fiducial plane, automatic multi-planar reconstruction of an oblique fiducial slice and on-the-fly update(s)

(Continued)

of template matching and registration error calculations based on user manipulation of detected fiducial locations.

24 Claims, 14 Drawing Sheets

(51) Int. Cl.
    *A61B 18/02*     (2006.01)
    *A61B 90/00*     (2016.01)
    *A61B 34/00*     (2016.01)
    *A61B 18/00*     (2006.01)

(52) U.S. Cl.
CPC .............. *A61B 90/37* (2016.02); *A61B 90/39* (2016.02); *A61B 2018/0022* (2013.01); *A61B 2018/00577* (2013.01); *A61B 2018/0212* (2013.01); *A61B 2018/0293* (2013.01); *A61B 2034/107* (2016.02); *A61B 2090/363* (2016.02); *A61B 2090/3762* (2016.02); *A61B 2090/3937* (2016.02)

(56) References Cited

U.S. PATENT DOCUMENTS

| | | | |
|---|---|---|---|
| 8,503,745 B2 | 8/2013 | Simon et al. | |
| 9,222,996 B2 | 12/2015 | Fujimoto et al. | |
| 9,867,673 B2 | 1/2018 | Onuma et al. | |
| 2005/0215879 A1 | 9/2005 | Chuanggui | |
| 2006/0004280 A1* | 1/2006 | Kotake | G06T 7/73 600/414 |
| 2008/0119712 A1 | 5/2008 | Lloyd | |
| 2015/0366620 A1 | 12/2015 | Cameron et al. | |
| 2016/0000515 A1 | 1/2016 | Sela et al. | |
| 2017/0000581 A1* | 1/2017 | Tokuda | G06K 9/6201 |
| 2017/0000582 A1 | 1/2017 | Fleig et al. | |
| 2017/0007349 A1* | 1/2017 | Solar | A61B 34/20 |
| 2018/0098819 A1 | 4/2018 | Onuma et al. | |
| 2018/0103979 A1 | 4/2018 | Arimitsu | |
| 2018/0228568 A1 | 8/2018 | Kato et al. | |
| 2019/0008591 A1 | 1/2019 | Desai et al. | |
| 2019/0035156 A1* | 1/2019 | Wei | A61B 34/10 |
| 2019/0046232 A1 | 2/2019 | Tokuda et al. | |
| 2019/0090953 A1 | 3/2019 | Nakamura | |
| 2019/0105109 A1 | 4/2019 | Kato | |
| 2019/0117317 A1 | 4/2019 | Abayazid et al. | |
| 2019/0151023 A1 | 5/2019 | Lu et al. | |
| 2019/0159844 A1 | 5/2019 | Daniels et al. | |
| 2020/0054378 A1 | 2/2020 | Kincaid et al. | |
| 2020/0121219 A1 | 4/2020 | Ganesan et al. | |
| 2020/0121287 A1 | 4/2020 | Nakamura | |

FOREIGN PATENT DOCUMENTS

| | | |
|---|---|---|
| JP | 2016-517321 A | 6/2016 |
| JP | 2018-149275 A | 9/2018 |
| JP | 2018-529399 A | 10/2018 |
| WO | 2017/010992 A1 | 1/2017 |
| WO | 2018/175094 A1 | 9/2018 |

OTHER PUBLICATIONS

David Driver, et al., "Improvements in radiotherapy practice: the impact of new imaging technologies", Cancer Imaging, vol. 4, Issue 2, Sep. 2004, pp. 142-150.

A. Gouze, et al., "Watershed-driven Active Contours for Moving Object Segmentation", Proceedings of IEEE International Conference on Image Processing (ICIP), vol. II, Genova, Italie, Sep. 2005, pp. 818-821 (four pages in PDF file).

U.S. Appl. No. 16/539,769, filed Aug. 13, 2019.

Tokuda, J., et al., "Integrated navigation and control software system for MRI-guided robotic prostate interventions", Comput Med Imaging Graph., vol. 34, No. 1, Jan. 2010, pp. 3-8 (http://www.ncbi.nlm.nih.gov/pmc/articles/PMC2815337/pdf/nihms163611.pdf) (14 pages in enclosed PDF file).

Liu, S., et al., "Automatic Multiple-Needle Surgical Planning of Robotic-Assisted Microwave Coagulation in Large Liver Tumor Therapy", Plos One, vol. 11, No. 3, Mar. 16, 2016, pp. 1-34.

* cited by examiner

VISUALIZATION AND MANIPULATION OF RESULTS FROM A DEVICE-TO-IMAGE REGISTRATION ALGORITHM

CROSS-REFERENCE TO RELATED APPLICATION(S)

This application relates, and claims priority, to U.S. Patent Application Ser. No. 62/747,913, filed Oct. 19, 2018, the entire disclosure of which is incorporated by reference herein in its entirety.

FIELD OF THE INVENTION

The present disclosure relates generally to the field of optical imaging, such as, but not limited to, in the field of interventional oncology, and more particularly to apparatuses, systems, methods and storage mediums for guidance of one or more medical instruments, such as needles used for minimally invasive puncture treatment, and for visualization and manipulation of device-to-image registration of such guidance apparatuses, systems, methods, and storage mediums. Examples of medical applications include imaging, evaluating and characterizing/identifying biological objects or tissue, such as, but not limited to, for identification, location and treatment of lesions/tumors, operation/procedure planning, simulation, ablation performance, biopsy performance, guiding needles or probes and visualization, manipulation and registration of guidance devices or systems.

BACKGROUND OF THE INVENTION

Minimally invasive medical procedures are becoming increasingly popular in the medical community due to shortened hospital stays and improved quality of life for the patient. For example, in the field of interventional oncology, percutaneous ablations are often preferred over surgical resection due to the minimally invasive nature of the procedure and thus shortened patient recovery period.

There are various forms of ablation, and successful ablation requires good planning. Ablation is normally ordered after diagnosis by oncologists who decide the ablation procedure is the best to treat a lesion/tumor. An interventional radiologist (IR) may be involved to gather and analyze images to accurately characterize tumors and their size and to review results from a biopsy procedure. However, diagnostic imaging is rarely good enough to plan with, so an IR may conduct initial imaging before developing/finalizing an action plan and starting an ablation procedure. The ablation strategy may include selection of an imaging modality in the procedure, probe insertion points, a number of probes and trajectories of the insertion, a modality of ablation such as microwave, cryo, etc., patient position during the procedure, coordinating with other clinicians (e.g., anesthetist, nurses, equipment technicians, etc.), etc.

Ablation takes a lot of planning, and there are a lot of variables. For example, clinicians in ablation planning try to figure out where is the target ablation zone including a lesion/tumor, where are the critical structures/features that must be avoided during the procedure, where is the target point in the target zone, what is the entry point on the body surface so that the probe can get into the body and reach a target point(s), what is the trajectory to connect an entry point to a target point while avoiding any critical structure/feature with consideration of needle orientation when scanning the body with the needle inserted, how many probes are needed to form an ablation zone, how big and what shape the ablation zone is, etc. When a lesion/tumor is identified and an ablation zone is defined, based on ablation probe type and quantities, clinicians normally use a visual overlay of the two zones to estimate the coverage zone, which tends to be inaccurate or be a less objective measure since it is a mental visual estimate.

Even though medical procedures (e.g., ablation, biopsy, needle guidance, etc.) are very complex, the procedure that is currently performed by clinicians is predominantly done manually and iteratively, which is error prone and may increase the time required to perform, for example, an ablation (i.e., be inefficient). Planning in particular is largely performed by clinicians with some help from basic visualization software. Clinicians typically start with reading Computed Tomography (CT) or Magnetic Resonance Imaging (MRI) scans, identify the target region and plan the insertion point and/or trajectory/orientation. For example, in at least one ablation planning scenario, clinicians load Digital Imaging and Communications in Medicine (DICOM) images of a patient into a computer and view 2D slice by slice of the CT or MRI scans of the patient. By going through the DICOM image slices, a clinician may construct a mental 3D model of internal anatomy of concern. By using the DICOM images, the clinicians may identify where the lesion/tumor is and may identify the relationship of the lesion/tumor and its surrounding critical structure, to determine the optimal probe entry point, target point and consequently the trajectory from the entry point to the target point.

During an image guided surgical procedure, an instrument such as a needle guidance device is manipulated relative to a patient. Medical images, such as CT images, MRI images, etc., may be used to plan the procedure, but the position of the instrument relative to the imaged anatomy must be determined to inform the surgical procedure. A registration or translation map must be generated to correlate the patient space, device space, and image space. In many applications in the medical field, accurate and precise positioning of medical instruments is critical. In the case of surgical procedures such as percutaneous intervention, exact placement of needle-like medical tools and instruments can mean the difference between success and failure of procedures.

Registration of patient, device, and image space may be performed. However, it is often difficult for the user to quickly and easily visualize and manipulate the results of registration.

Once a medical device, such as a guidance device, is registered and positioned on a patient or over a target area of a body of the patient, the clinicians may identify the entry point on the surface of the body that corresponds to what the clinicians envisioned in the image scans. The clinicians may perform a test drive to insert a needle a little bit, perform a scan, and find the difference between the actual needle insertion demonstrated by the scan and what was expected before the insertion. This gives the clinicians a chance to make any correction if necessary. This step may be repeated several times for the needle to finally reach the target point.

Typically, where the medical procedure is ablation, a target point is in a center of the lesion/tumor in a case where a single probe is used. Clinicians may use a pointing device such as a mouse or touch point to mark a location in the center of the lesion/tumor which is shown in the basic visualization software. Clinicians may either place a probe tip to allow ablation to occur, or may implant seeds for radio/chemo therapy. Even the marking process is manual and approximate in nature. In 2D, marking a center position for an object may not be hard, even though many times it may not be accurate due to human visual and motor action inaccuracy/error. However, a clinician using 2D slice view to figure out a center of a 3D volume which includes a stack of 2D slices may be difficult and error prone if the center of the volume is the target point, and the clinician may be tricked by image artifacts and/or human limitation in 3D reasoning. In 3D, marking a center position is much harder because of the intricate limitation of visualization/rendering software. Relying on clinicians' intuition, experience and visual understanding to define a target point is not optimal (for reliability, repeatability, traceability, etc.), particularly in 3D space. When the lesion/tumor has a very complicated shape, defining an appropriate target is more or less an art, and it is difficult to achieve consistency.

If multiple needles are needed to make the ablation zone large enough to cover the target zone, clinicians typically use a first needle as reference, and plan the next needles based on the result from the first or previous needle insertion and/or ablation. If there are multiple needle insertions needed, cases are done mostly in an incremental fashion— for example, plan, insert a needle, scan, make an adjustment or modification to the original plan (if needed) based on the scan of the inserted needle, insert another needle, etc.

Devices/hardware is also lacking to help clinicians aid in the insertion of multiple probes or needles and in the registration of such guidance devices, probes and/or needles during a procedure, such as, but not limited to ablation, biopsy, or other procedures.

In current practice, as aforementioned, needles or other devices, such as ablation probes, are guided in a free-handed manner using medical imaging for guidance. It is very difficult to achieve these preset needle or probe configurations with this approach and thus an improved guidance, visualization and/or registration method is needed. Clinicians employ incremental insertion movement by trial and error to deal with the inevitable organ movement and deformation (e.g., as aforementioned, a clinician may insert a needle a little, scan, read the image(s) to find out how much the needle is off, adjust or change the needle trajectory if needed or keep going, if the target point is moved during probe insertion, etc.). Currently, a first probe insertion is made and scanned to use the scan as a reference. Then subsequent incremental insertions of the probe may be made towards the target with scans after each insertion to assess same. Such a process may include repositioning the patient if needed to make insertion more controllable. Additionally, an IR or clinician may assume the probe is rigid and that organs have no deformation and movement from now until the insertion. Alternatively to scanning, an ultrasound transducer along with the ablation probe may be used to guide the probe into the planning direction to reach the target, which requires ultrasound image fusion with CT/MRI (CT fluoroscopy is another technique that may be used with CT during planning and performance of ablation). This not only increases the procedure time, but also wastes a lot of efforts in adjustment/making changes. Of course, it is also likely having impact(s) on or causing possible damage to nearby structure and tissues. Considering organ movement and deformation may make medical procedure planning and performance more complex, and may hamper interaction between clinicians and ablation planning and performance devices. The reality is that many factors (e.g., breathing, body movement or pose change, organ deformation due to interaction with the probe, etc.) affect probe insertion and may change between planned insertion and actual insertion. Such changes may also invalidate the planned insertion. Respiratory gating, or asking patients to hold their breath, is time consuming monitoring techniques that may be used to assist with insertion. Modeling organ deformation is another way to try to anticipate movement and deformation issues with insertion. However, such procedures do not guarantee success or efficiency. Ultimately, the purpose of probe registration and insertion is to perform or conduct a medical procedure (e.g., biopsy, ablation, etc.), and procedures are needed to reduce and/or avoid the aforementioned issues with needle insertion. Once the needle or probe is setup properly, the procedure is thereafter performed.

In view of the above, there is a need for software and/or hardware to provide clinicians with help to make visualization, manipulation and registration more efficient (e.g., reduce procedure time), more accurate, and more effective (including, but not limited to, more cost-effective (cheaper), optimized for lesion/tumor removal, etc.), in addition to providing enhancement in visualization, manipulation and/or needle or probe guidance/placement. There is a need for an intuitive way to present the registration results to the user which allows for confirmation and optional corrections to improve the registration. There is also a need for a method for visualization of registration results, and/or a method to intuitively manually manipulate the registration results to confirm and/or optimize registration and reduce error.

SUMMARY OF THE INVENTION

One or more systems, devices, methods and storage mediums are provided herein, including, but not limited to, apparatus(es), system(s) or device(s), and methods and storage mediums for guiding multiple needles or ablation probes and/or for visualization and manipulation of results from a device to image registration algorithm. In the medical environment, in one or more applications, it is necessary to position a needle or multiple needles, or a probe or multiple probes, precisely inside and/or on tissue or a specific organ for accurate diagnosis or minimally invasive procedure(s), such as, but not limited to, therapy, treatment, etc.

One or more embodiments of the present disclosure relate to one or more medical devices, methods and storage mediums for holding and positioning a needle or needles, or a probe or multiple ablation probes, in desired geometric configurations and/or for visualization and manipulation of results from a device to image registration algorithm.

One or more embodiments provide useful hardware for physically guiding planned needles along planned trajectories, and/or for visualization and manipulation of results from a device to image registration algorithm.

In at least one embodiment, automatic multi-planar reconstruction of a device fiducial plane may be given to provide a user with a quick and intuitive method to visualize results of an automatic device-to-image registration algorithm. For example, one or more embodiments may include one or more of the following: an overlay of automatic registration detected fiducial locations and an overlay of slice intersections of a template matched virtual model of the device and corresponding fiducials. The device fiducial plane reconstruction may present all imaged fiducials of the device with an overlaid representation of the virtual device model slice intersections as well as a representation of the detected fiducial locations. User manipulation of the detected fiducial locations, such as, but not limited to, adding, moving, and/or deleting fiducials, is possible with such device fiducial plane reconstruction which drives a re-registration of the virtual model with the fiducial locations.

In at least one or more embodiments, automatic multi-planar reconstruction of an oblique fiducial slice may be provided. Upon user selection of a fiducial, the oblique slice may be automatically reconstructed provided a third dimension (3D) of registration. The oblique fiducial slice reconstruction may present all imaged fiducials of the device with overlaid representation of the virtual device model slice intersections as well as a representation of the detected fiducial locations. The oblique slice may allow the user to assess the virtual model matching to detected fiducial locations in the third dimension of the image. User manipulation of the detected fiducial locations, such as, but not limited to, adding, moving, and/or deleting fiducials, may be possible on this oblique fiducial slice reconstruction which drives a re-registration of the virtual model with the fiducial locations.

In at least one or more embodiments, on the fly (e.g., when needed, in real time, manual, automatic, during a medical procedure, while in progress, etc.) update(s) of template matching and registration error calculations based on user manipulation of detected fiducial locations (e.g., such as, but not limited to, adding, deleting, and/or moving fiducial locations) may be provided. As such, a user may receive, or be provided with, immediate feedback on how the user manipulation of detected fiducial locations affects the registration, and/or affects the matching of the virtual model and imaged fiducials (aka template matching), providing an intuitive method for the user to optimize the registration.

In one or more embodiments, percutaneous ablation procedures involve the physician having to guide ablation probe(s) to a target of interest, such as an area of interest (e.g., a tumor, a nodule, a lesion, etc.), deep in the body with the aid of medical imaging (e.g., CT, MRI, Ultrasound, other scanning devices, etc.). For example, various ablation modalities exist (radiofrequency, microwave, cryo, laser, and irreversible electroporation). The physician selects the needle(s) or probe(s) which will be able to perform a desired medical procedure (e.g., fully ablate a tumor along with a safety margin surrounding the tumor to reduce the risk of tumor recurrence). In some cases, a single needle or probe may not be enough to achieve the desired procedure (such as, but not limited to, achieve full tumor coverage), and thus multiple needles or probes may be used (e.g., for a larger ablation zone to ensure full tumor coverage). Moreover, there is often a preset probe configuration that is desired in each ablation modality. For example, in microwave and irreversible electroporation a parallel probe configuration is desired. In the parallel probe configuration, probes are guided parallel at a preset maximum distance. The pre-set maximum distance ensures a larger uniform ablation zone. Exceeding the maximum probe distance may result in independent ablation zones around each probe and thus lead to missed tumor cells between probes causing or leading to tumor recurrence. In cryo-ablation, many physicians prefer to bracket the tumor in a conical probe arrangement in order to ensure all insertion points of the probes are in close proximity. Sharing a close insertion point for all probes in cryo-ablation is desired so that the physician can more easily protect the skin from cryo burns by applying warm saline around the probe insertion points. In one or more embodiments, drug delivery and/or treatment may also be performed in addition to one or more of biopsy, ablation, therapy (e.g., cryotherapy), aspiration, etc. One or more embodiments of the present disclosure provide configurations and processes for achieving guidance and placement of needle(s) and/or probe(s) to perform a desired minimally invasive procedure(s), including using one or more methods for visualization and manipulation of results from device-to-image registration to improve or optimize placement of the needle(s) and/or probe(s).

In one or more embodiments, an apparatus and a method for a medical guidance device may include a base assembly including a base ring or a fixed portion having an inner circumference defining an opening, and a guide or moving portion rotateably mateable with the base assembly, the guide having a frame with an inner circumference defining an opening and an outer circumference, wherein, in a configuration where the guide is mated with the base assembly, the opening of the frame overlays the opening of the base ring. The medical guidance apparatus also has an arc member (and may, in one or more embodiments, have a holder slideably attached to the arc member, wherein the holder is configured to hold a medical tool intended to be guided by the medical guidance apparatus). Preferably, in one or more embodiments, the fiducial markers are located or disposed in the base assembly (e.g., in a base ring or fixed portion, portion attached to a patient, in the rotateably mateable guide or moveable portion, etc.).

In one or more embodiments, the arc member comprises a guidance surface, wherein the guidance surface comprises one or more angular reference marks. The angular reference marks may be used to align with an indicator configured upon the arc member guidance surface to accurately situate the holder in the desired angular position (especially after the guide device is registered). In further embodiments, the medical guidance apparatus comprises a gap extending from the inner circumference of the frame to the outer circumference of the frame, to allow for detachment and/or reattachment of the medical guidance apparatus to the surface without interrupting the medical tool.

In additional embodiments, the holder further comprises a groove for accepting the medical tool and a door for holding the medical tool in the holder. Furthermore, the door may be hingedly attached to the holder, and further comprises a tab, configured to align with the groove on the holder, to aid in holding the medical tool in the holder. In other embodiments, the door may be removable and/or replaceable.

One or more further embodiments of the subject disclosure include a method of guiding a medical instrument, comprising, mounting a medical guidance apparatus about a predetermined insertion point of a surface, the medical guidance apparatus comprising a base assembly including a base ring having an inner circumference defining an opening and a guide rotateably mateable with the base assembly, the guide including a frame having an inner circumference defining an opening and an outer circumference, wherein, in a configuration where the guide is mated with the base assembly, the opening of the frame overlays the opening of the base ring. The apparatus may further include an arc member and a holder slideably attached to the arc member, wherein the holder is configured to hold a medical tool intended to be guided by the medical guidance apparatus. The method may further include positioning the guide to a predetermined position relative to the base ring, positioning the medical instrument to a predetermined position upon the holder, and inserting the medical instrument through the insertion point.

The present disclosure, via one or more embodiments, achieves fundamental needle or multi-needle, or probe or multi-probe, configurations desired for procedures, such as, but not limited to, ablations, biopsy, diagnosis, treatment, etc., without multiple interchangeable probe guides.

One or more other features discussed herein may reduce the risk of user error.

One or more features of one or more embodiments of the present disclosure may be used for various types of devices, such as, but not limited to, an MRI, Ultrasound or other scan devices instead of a CT scanner. One or more embodiments may be able to apply any position detectors instead of an encoder. One or more embodiments may use a speaker, vibrator or other lighting devices instead of light emitting diodes (LEDs) to help guide, manipulate and/or register a device, probe and/or needle. While ablation procedures are discussed above as one or more examples of needle guidance and placement, one or more embodiments may apply biopsy needles or other medical procedure needles instead of ablation needles.

In accordance with one or more embodiments of the present disclosure, needle guidance planning and performance and/or visualization and registration apparatuses and systems, and methods and storage mediums may operate to characterize biological objects, such as, but not limited to, lesions, tumors, critical structures, etc.

In accordance with at least another aspect of the present disclosure, the ablation probe or needle placement/guidance and/or visualization, manipulation and registration technique(s) discussed herein may be employed to reduce the cost of at least one of manufacture and maintenance of ablation planning and performance devices, systems and storage mediums by reducing or minimizing a number of components therein to cut down cost.

According to other aspects of the present disclosure, one or more additional apparatuses, one or more systems, one or more methods, and one or more storage mediums using visualization and registration technique(s) are discussed herein. Further features of the present disclosure will become apparent from the following description of exemplary embodiments with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE PRESENT INVENTION

One or more devices, systems, methods and storage mediums for performing guidance for needles or probes and/or for visualization and manipulation of result(s) from device-to-image registration are disclosed herein. In one or more embodiments, the configurations, methods, apparatuses, systems and/or storage mediums may be combined to further enhance the effectiveness in guiding the needles or probes, including using one or more methods for visualization and manipulation of results from device-to-image registration to improve or optimize placement of the needle(s) and/or probe(s). Several embodiments of the methods, which may be carried out by the one or more embodiments of an apparatus, system and computer-readable storage medium, of the present disclosure are described diagrammatically and visually in FIGS. 1 through 14.

Figure 1:
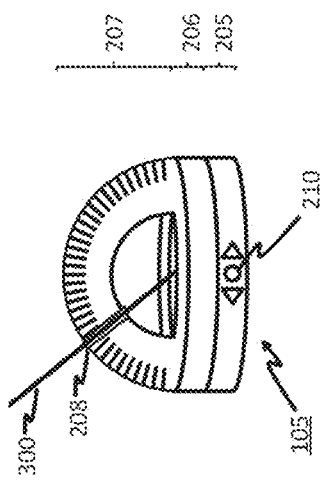
FIG. 1 is a schematic diagram showing an embodiment of a guidance device and/or system for performing needle guidance in accordance with one or more aspects of the present disclosure.
Figure 2A:
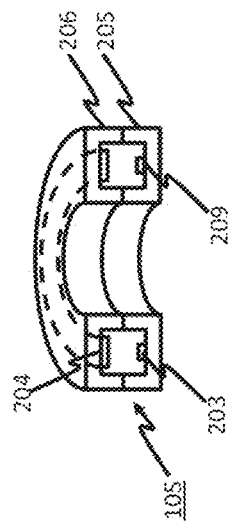
FIG. 2A is a schematic diagram showing a section view of the guidance device and/or system of FIG. 1 in accordance with one or more aspects of the present disclosure.
Figure 2B:
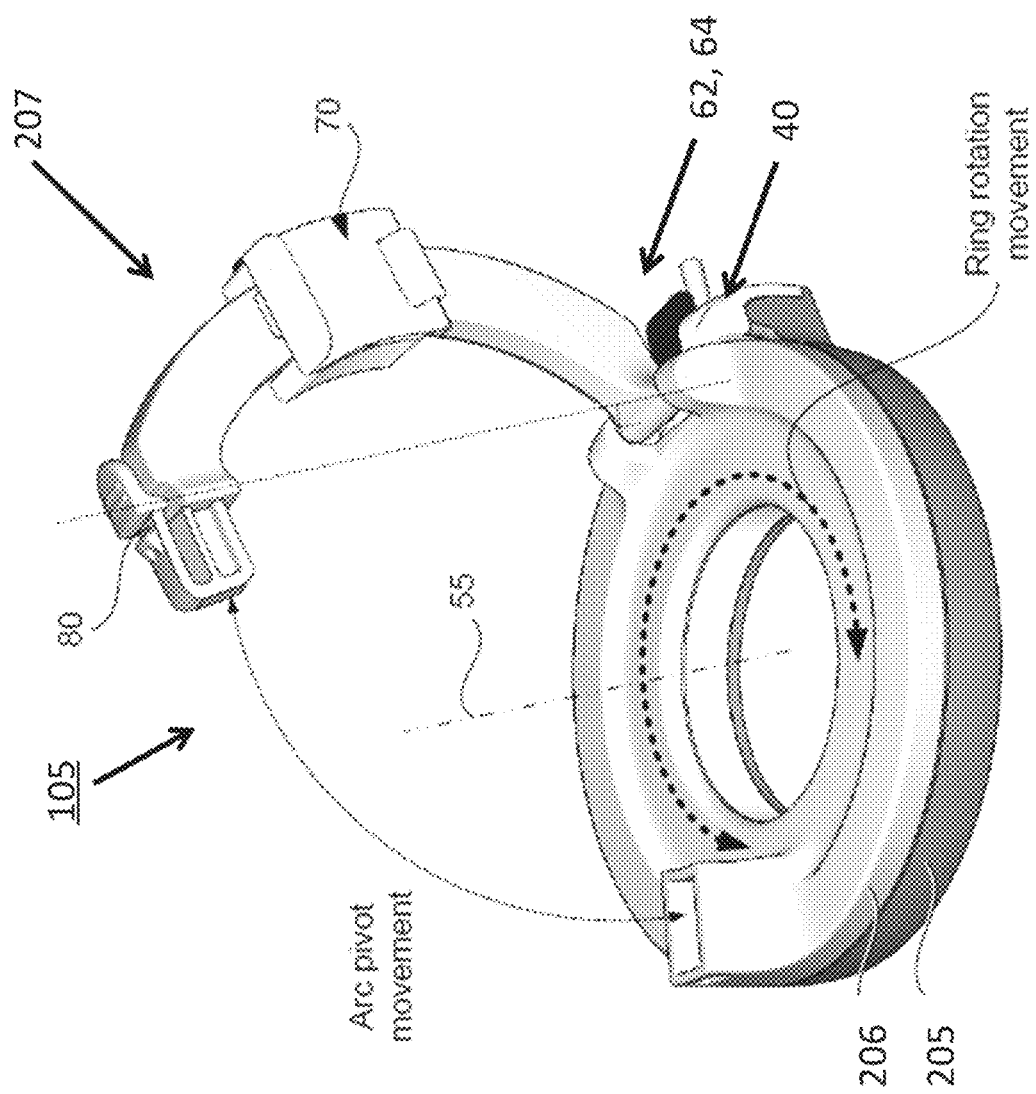
FIG. 2B is a schematic diagram showing an alternative embodiment of a guidance device and/or system in accordance with one or more aspects of the present disclosure.

In accordance with at least one aspect of the present disclosure, at least one embodiment of a device for guiding needles or probes, and for performing visualization and manipulation of results from a device-to-image registration, may include structure from one or more embodiments as shown in FIGS. 1-2B. In FIG. 1 there is a guidance device 105, which preferably includes a fixed part 205 and a movable part 206. The guidance device 105 may include a processor 1201, 1201' (while reference number 1201' is used to indicate a "second" processor, the structure discussed herein and shown in the accompany figures for the processor or CPU 1201 may be used in one or more embodiments of the guidance device 105), a wireless or wired communication circuit 1205, 1212 (while reference numbers 1205 and 1212 refer to a communication interface and a network interface, respectively, as discussed below, the structure for both elements 1205 and 1212 may be used for the wireless or wired circuit in one or more embodiments of the guidance device 105), and an encoder sensor 203. The guidance device 105 may further include, or be used with, one or more fiducial markers 209, one or more light emitting diodes (LEDs) 210, and/or one or more batteries in one or more embodiments. A plurality of fiducial markers 209 may be included (embedded) in the device 105 (e.g., in the fixed part 205, in the movable part 206, etc.) for device to image (or device-to-image) registration.

In one or more embodiments, the movable part 206 may include an encoder scale 204. The encoder scale 204 may be fixed on the movable part 206. In one or more embodiments, the fixed part 205 and the movable part 206 are removably attached to each other such that the encoder sensor 203 faces or is disposed towards the encoder scale 204 in a case where the fixed part 205 and the moveable part 206 are attached as best seen in FIG. 2A. Alternatively, in one or more embodiments, the encoder scale 204 may be fixed on the fixed part 205, and the encoder sensor 203 may be disposed on the movable part 206 to achieve positional sensing between the fixed part 205 and the moveable part 206.

In one or more embodiments, the encoder sensor 203 operates to detect a relative position with respect to (and/or based on interaction with or sensing) the encoder scale 204. In embodiments where the encoder sensor 203 is fixed on the fixed part 205, relative displacement between the fixed part 205 and the movable part 206 may be detected by the encoder sensor 203 and/or an encoder.

Preferably, in one or more embodiments, the movable part 206 further includes an arc 207 as best seen in FIG. 1. A needle holder 208 is preferably attached on, or may be used with, the arc 207. Preferably, the needle holder 208 is movable along the arc 207, and the needle holder 208 operates to hold a needle by one or more methods, including, but not limited to, friction, pressure fitting, a clasp or grasping mechanism, etc. Preferably the arc 207 includes a scale (e.g., a tool for measuring an angle of the needle or other item being held by the holder 208) so that a user of the device or system 105 may read an angle at which the needle or other item being held by the holder 208 is oriented. In one or more embodiments, the arc 207 may be releasably connected to the movable part 206 such that the arc 207 may be released from the movable part 206 as needed. In one or more embodiments, the arc 207 may be integral with the movable part 206.

Preferably, in one or more embodiments of the device or system 105, fiducial markers 209 (see e.g., the fiducial marker 209 shown in FIG. 2A; see also, one or more of F-1 through F-8 in FIGS. 4-6) may be used for registration of the device or system 105. Because fiducial markers 209 are visible in CT images, a processor, such as a first processor 1201 of a computer 2, 2' (see e.g., FIG. 7 as discussed further below, and FIGS. 12-13 as discussed further below, etc.) and/or the second processor 1201, 1201' of the guidance device or system 105, may calculate an orientation of the guidance device 105 based on the positions of a plurality of the fiducial markers 209, F-1 through F-8, etc. In one or more embodiments, fiducial markers 209, F-1 through F-8, etc. may be implanted in the fixed part 205 and placed uniquely in a three dimensional (3D) space. Other types of fiducial markers may be used in one or more embodiments of the present disclosure. For example, fiducial markers (and methods, apparatuses and systems related to same) discussed in U.S. patent application Ser. No. 15/727,978, filed Oct. 9, 2017, the entirety of which is incorporated by reference herein, and as discussed in U.S. Pat. Pub. No. 2019/0105109, published on Apr. 11, 2019, the entirety of which is incorporated by reference herein, may be used in one or more embodiments.

An insertion angle of a needle 300 (e.g., one or more needles use for a medical procedure as discussed herein, such as, but not limited to, ablation, biopsy, etc.) is preferably guided by a combination of the scale on the arc 207, a position of the encoder sensor 203 and orientation of the guidance device or system 105 in one or more embodiments. If a user places the guidance device or system 105 on a designated or predetermined or predefined position, then the fiducial markers 209 may be optional or may not be used as needed. In such a step, a processor, such as the first processor 1201 of a computer 2, 2', the second processor 1201, 1201' of the guidance device 105, etc., does not need to calculate orientation in view of the preset orientation. That said, as further discussed below, preferably one or more embodiments of methods for visualization and manipulation of device-to-image registration use fiducials.

In one or more additional embodiments, the guidance device or system 105 may include additional or alternative features as discussed in U.S. Provisional Patent Application No. 62/764,849, filed on Aug. 15, 2018, the entirety of which is incorporated by reference herein, may include additional or alternative features as discussed in U.S. Provisional Patent App. No. 62/764,820, filed Aug. 15, 2018, the entirety of which is incorporated by reference herein, may include additional or alternative features as discussed in U.S. Provisional Patent App. No. 62/875,243, filed Jul. 17, 2019, the entirety of which is incorporated by reference herein, and may include additional or alternative features as discussed in U.S. patent application Ser. No. 16/539,769, filed Aug. 13, 2019, the entirety of which is incorporated by reference herein. For example, FIG. 2B illustrates a perspective view another embodiment of a medical guidance device or apparatus 105 having a guide or upper movable portion 206, a fixed portion 205, and an arc 207 using a hinge assembly 62, 64 (e.g., the arc 207 may be terminated at one end thereof with a hinge, such as, but not limited to, a c-shaped clip 62 to be disposed on, around or over a pin 64) where the hinge assembly 62, 64 is, for example, in an opened position or state. The fixed portion 205 and the moveable portion 206 are similar to a base assembly (e.g., the base assembly 2110) and a guide or upper movable portion (e.g., the guide or upper movable portion 2150), or the other base assembly no and the upper movable portion 150 of a guidance device or apparatus as discussed in U.S. Provisional Patent Application No. 62/764,849, as discussed in U.S. Provisional Patent Application No. 62/875,243, as discussed in U.S. Provisional Patent App. No. 62/764,820, and/or as discussed in U.S. Patent Application Ser. No. 16/539,769, the entireties of which applications are incorporated by reference herein (similar reference numbers represent corresponding features). In this configuration (best seen in FIG. 2B), the other end of the arc 207 has been un-clipped from the rotating ring of the moveable portion 206 and the entire arc 207, including the probe holder 70 (which is similar to other probe or needle holders, such as those discussed in U.S. Provisional Patent Application No. 62/764,849, discussed in U.S. Provisional Patent Application No. 62/875,243, discussed in U.S. Provisional Patent App. No. 62/764,820, and/or discussed in U.S. patent application Ser. No. 16/539,769), is removed out of an insertion path 55. In the open position, the arc 207 may be positioned in one or more orientations, for example, substantially perpendicular to a plane of the ring of the moveable portion 206 or the fixed portion 205. However, if more space is needed for access to the area of interest, the first end of the arc 207 may also be detached at the pivotable hinge assembly 62, 64. To that end, the pivotable hinge assembly 62, 64 may be designed in other ways known to those skilled in the art such that the hinge assembly 62, 64 operates to pivot as a hinge, and is not limited to the c-shaped clip 62 and pin 64 configuration. This design allows the guide device (guidance system) 105 to be used in a variety of interventional and/or medical procedures.

For example, during a needle insertion procedure, it is highly advantageous that the arc 207 is rigidly attached at both ends thereof to the ring moveable portion 206 (e.g., as shown in at least FIG. 1). However, either before or after needle insertion procedure, the arc 207 may be entirely separated (removed) from the ring of the moveable portion 206. As mentioned above, the fixed portion 205 is configured to be strapped onto the patient's body to avoid accidental movement. Therefore, at the beginning of a procedure, only the fixed portion 205 and the ring of the moveable portion 206 may be attached to the patient's body to give the physician the opportunity to arrange the guide device 105 on the precise location of needle insertion.

On the other hand, after a needle insertion procedure is completed, e.g., after a first needle has been inserted, the physician may need to access the insertion point for inspection or confirmation. In that case, the arc 207 may be unlocked from the ring of the moveable portion 206 by operating the snap joint locking mechanism 80, and then the arc 207 is pivotably rotated to the position shown in FIG. 2B. This gives access to the physician for the necessary observation and confirmation of needle insertion. In addition, if more room is necessary for access to the insertion area of interest, the arc 207 may be disengaged from the pin 64 (e.g., the c-shaped clip 62 may be disengaged from the pin 64) of the ring of the moveable portion 206 so that the entire arc 207 and the needle holder 70 may be removed from the ring of the moveable portion 206 and/or the moveable portion 206. However, even after the arc 207 and needle holder 70 are removed, the fixed portion 205 and the ring of the moveable portion 206 and/or the moveable portion 206 may still remain rigidly attached to the patient's body. To that end, a latch cam 40 may be provided at any position along the circumference of the ring of the moveable portion 206 to maintain the ring of the moveable portion 206 and/or the moveable portion 206 in a fixed (anti-rotating) position.

Therefore, in the event that a new needle-insertion procedure is being performed on the patient, e.g., in the case of having to use multiple needle-like instruments, the arc 207 including the needle holder 70 may be simply mounted back onto the ring of the moveable portion 206 and/or to the moveable portion 206 by engaging the pivotable hinge assembly 62, 64 (e.g., by reconnected the hinge clasp 62 to the pin 64) and click-mounting the arc locking mechanism 80. In this manner, this pivotable and removable arc 207 and the needle holder 70 may provide at least: (i) ease of access to the area of interest, (ii) stiff and rigid support for needle-like instrument insertion, (iii) precise guidance during instrument insertion, and (iv) effective repeatability of insertion because the fixed portion 205 and the ring of the moveable portion 206 and/or the moveable portion may remain rigidly attached to the patient's body at all times during a medical procedure.

One or more embodiments provide useful hardware for physically guiding planned needles along planned trajectories, and/or for visualization and manipulation of results from a device to image registration algorithm. Indeed, prior to performance of such medical procedures, it is useful to accurately position the guidance device 105, and one or more embodiments discussed herein allow a user of the guidance device 105 to visualize results of an automatic registration and to manipulate such results as discussed below.

Figure 7:
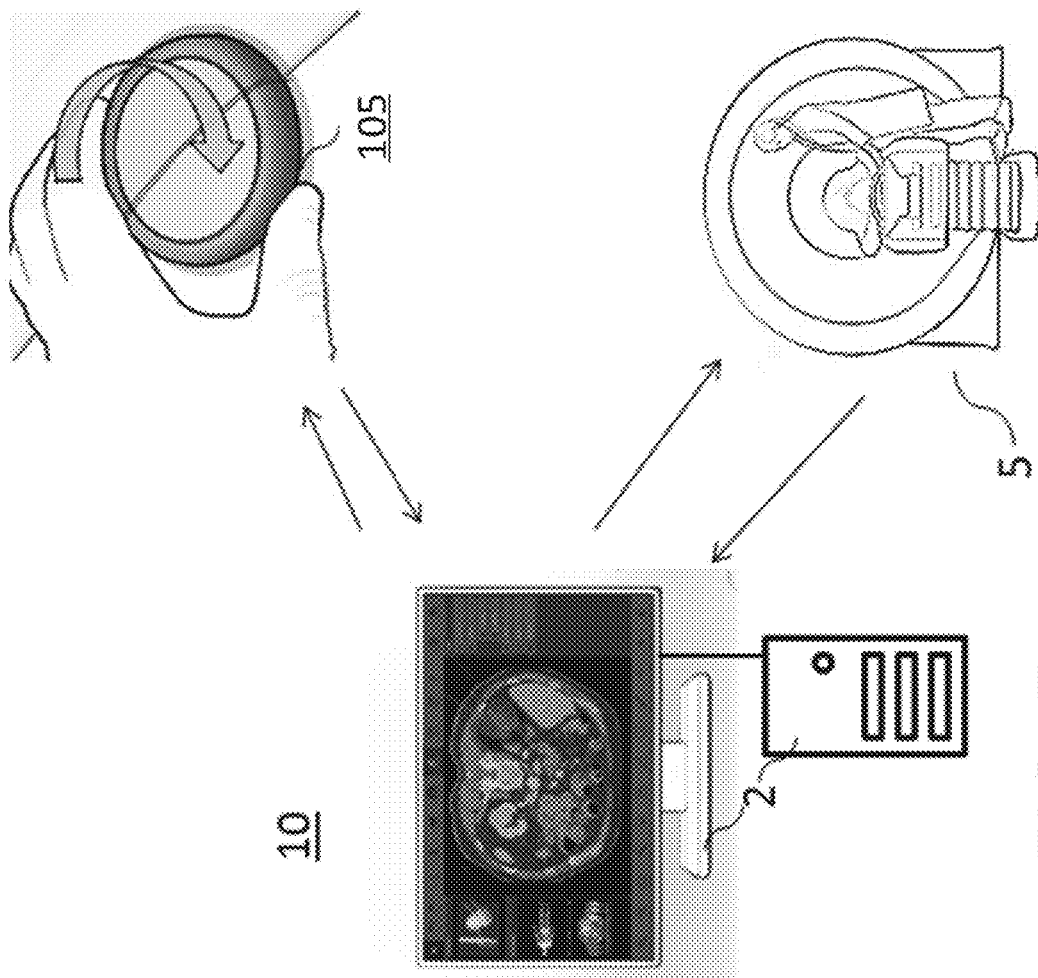
FIG. 7 is a schematic diagram showing an embodiment of a system for performing ablation and/or needle guidance planning and/or performance in accordance with one or more aspects of the present disclosure.
Figure 7:
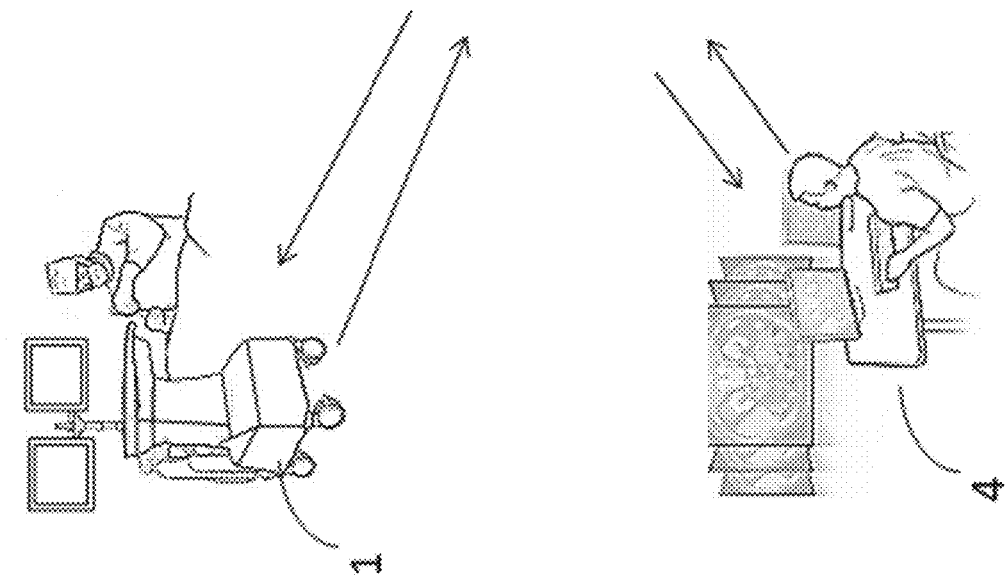

In one or more embodiments of methods for visualizing and manipulating registration results, the method(s) may include one or more visualization and manipulation steps, including, but not limited to, one or more of the following: (i) obtaining a medical device (see e.g., medical device 1 as shown in FIG. 7, a guidance device 105 as shown in FIGS. 1-2B and 7, etc.) (see step S101 in FIG. 3); (ii) acquiring and/or loading images (e.g., from a scanner, a PACS or other scanning device/system, or using a fresh or newly scanned image) (see step S102 in FIG. 3); (iii) performing automatic registration (e.g., detect fiducial locations)(see step S103 in FIG. 3); (iv) matching detected fiducial locations to a template (e.g., a virtual CAD model of the device 105 with known fiducial locations) and calculating registration error (if any) (see step S104 in FIG. 3); (v) reconstructing the detected fiducial plane (e.g., the plane obtained from the registration algorithm, the plane obtained from the automatic registration algorithm, etc.) through multi-planar reconstruction (see step S105 in FIG. 3); (vi) reconstructing (e.g., manually or automatically) an oblique slice through each detected fiducial (e.g., fiducial markers 209, fiducials F-1 through F-8, etc.) and/or overlaying the detected fiducial location points (see step S106 in FIG. 3); (vii) overlaying the detected fiducial locations on some or all reconstructed images (see step S107 in FIG. 3); (viii) reconstructing (e.g., manually or automatically) an oblique slice through each detected fiducial (e.g., fiducial markers 209, fiducials F-1 through F-8, etc.) (see step S108 of FIG. 3); (ix) calculating registration error (if any) and determining whether the registration error is acceptable or optimized and/or whether registration looks visually correct (see step S109 in FIG. 3); (x) in the event that the registration error acceptability is "NO" (step S109), then the user adds, deletes and/or moves detected fiducial point(s) in reconstructed images (see step S110 in FIG. 3); and (xi) in the event that the registration error acceptability is "YES" (step S111), then the user performs registering the device space to the image space (see step S112 in FIG. 3).

Preferably, in step S101, the obtained device (e.g., the guidance device 105) has all fiducials 209, F-1 through F-8, etc. physically located in a single plane of the device 105. Obtaining the medical device may include, for example placing or securing the device 105 onto the patient over a surgical site.

Preferably, in step S102, medical image data is obtained of the device 105 on the patient. The image data may be, for example, MRI or CT data.

The fiducial marker (e.g., fiducial markers 209, fiducials F-1 through F-8, etc.) objects from the medical image data may be detected by an automatic registration algorithm in one or more embodiments (see step S103).

In one or more embodiments of step S104, detected fiducial locations may be matched to a virtual CAD model of the device 105 with known fiducial locations, and registration error may be calculated. The registration error value may be calculated as the mean square distance of the closest points between the detected fiducial markers (e.g., fiducial markers 209, fiducials F-1 through F-8, etc.) in the images and the template matched virtual model fiducial locations.

In one or more embodiments of step S105, the fiducial plane detected by the automatic registration algorithm may be reconstructed through multi-planar reconstruction. In one or more embodiments, the fiducial plane reconstruction is a plane such that all fiducials are shown in a single two dimensional (2D) image.

In one or more embodiments of step S106, algorithm detected fiducial locations may be overlaid on some or all reconstructed images. Fiducial locations may, for example, be indicated by an overlaid dot 301 on the images (best seen in FIGS. 5-6).

In one or more embodiments of step S107, a representation of virtual device model mounted fiducials matched to algorithm detected fiducial positions may be overlaid on some or all of the reconstructed slices. Slice intersections of the virtual model mounted fiducials may be, for example, an outline of the solid model of each fiducial on the reconstructed slice 302 (best seen in FIGS. 5-6).

In one or more embodiments of step S108, an oblique slice through each detected fiducial also may be reconstructed automatically. Oblique slices may provide the $3^{rd}$ dimension of fiducial location. Alternatively, one or more embodiments of a method for visualizing and manipulating registration results may be performed without step S108. For example, step S105 may reconstruct the plane that contains all fiducials. Step S106 may overlay points on that image where fiducials have been detected. Step S107 may overlay the outlines of the device for visual identification of how well, accurately or closely the model matches. While step S108 may reconstruct a slice perpendicular to the reconstructed slice from step S107 so that a user may adjust the detected fiducial location in the third dimension (e.g., perpendicular to the reconstructed slice; substantially perpendicular to the reconstructed slice; etc.). However, in one or more embodiments not using step S108, the updating of the detected fiducial locdations may instead occur in the slice reconstructed or constructed in step S105.

In one or more embodiments, the calculated registration error (from step S104) and the visual representation of registration through auto reconstructed slices (from steps S105 and S106) allow for quick and intuitive visualization of the automatic device-to-image registration algorithm results.

Figure 3:
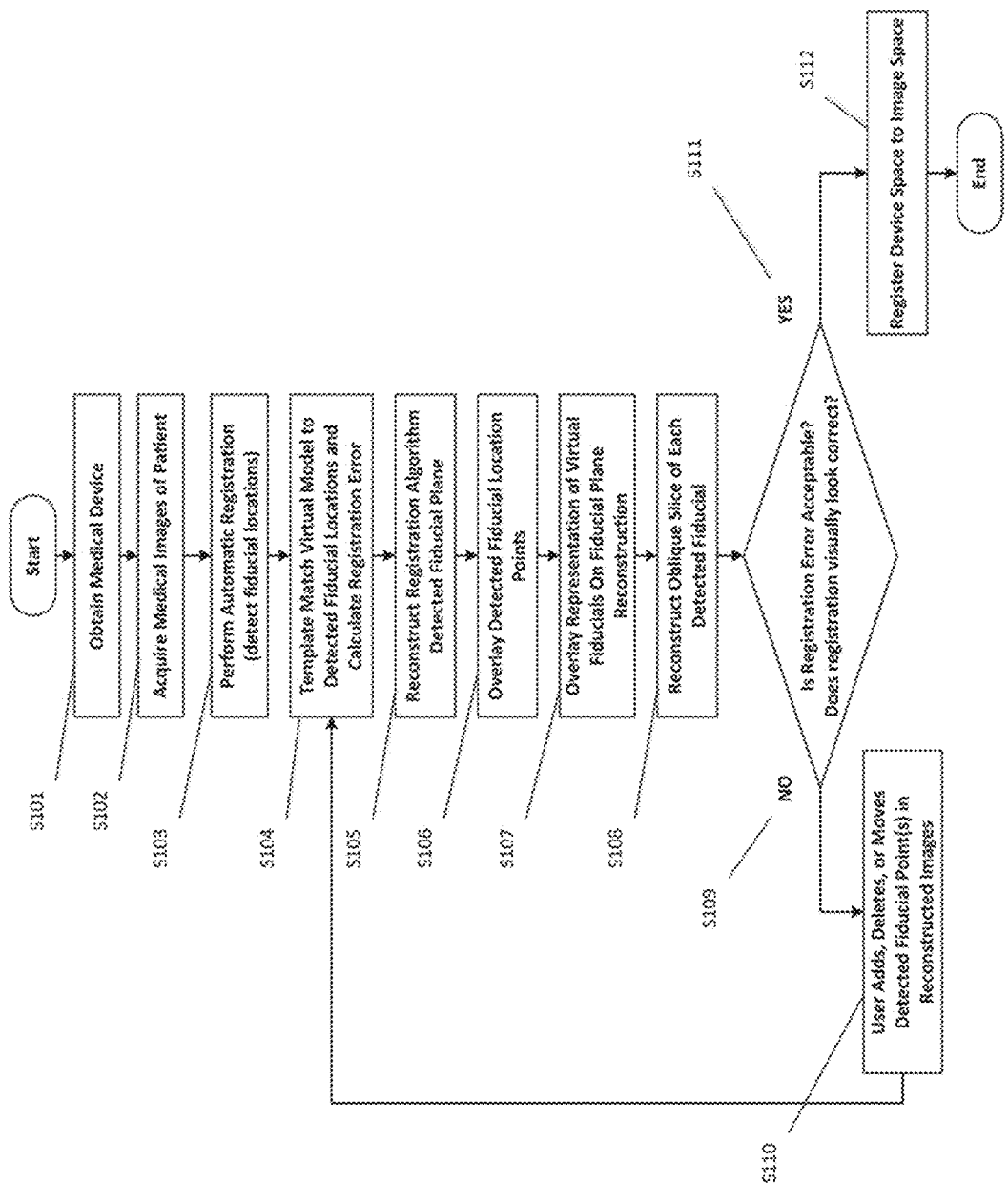
FIG. 3 is a flow chart of at least one embodiment of a method to visualize and manipulate results from an automatic registration algorithm in accordance with one or more aspects of the present disclosure.

In one or more embodiments of step S109 and/or step S1*ll*, the user then decides whether registration is optimized or not. If there are clear mismatches between image locations of fiducials and the matched virtual model made visually apparent by the automatically generated slice reconstructions, then the user would perform step S110 and add, delete, and/or move overlaid detected fiducial locations, which would trigger a recalculation of the template match of the virtual fiducial device model and detected fiducial locations (see return to step S104 as best seen in FIG. 3). In such a situation where there are multi-planar slice reconstructions, steps S105 and S106 are then updated and fiducial locations (see step S107) and virtual model fiducial slice intersections (step S108) would be re-drawn. The process continues until the user is satisfied with the registration results, and, once the user is satisfied, the user follows the path to step S112 to complete the registration process.

In at least one embodiment, automatic multi-planar reconstruction of a device fiducial plane may be provided to provide a user with a quick and intuitive method to visualize results of an automatic device-to-image registration algorithm. For example, one or more embodiments may include one or more of the following: an overlay of automatic registration detected fiducial locations and an overlay of slice intersections of a template matched virtual model of the device and corresponding fiducials. The device fiducial plane reconstruction may present all imaged fiducials of the device with an overlaid representation of the virtual device model slice intersections as well as a representation of the detected fiducial locations. User manipulation of the detected fiducial locations, such as, but not limited to, adding, moving, and/or deleting fiducials, is possible with such device fiducial plane reconstruction which drives a re-registration of the virtual model with the fiducial locations.

In at least one or more embodiments, automatic multi-planar reconstruction of an oblique fiducial slice may be provided. Upon user selection of a fiducial, the oblique slice may be automatically reconstructed provided a third dimension (3D) of registration. The oblique fiducial slice reconstruction may present all imaged fiducials of the device with overlaid representation of the virtual device model slice intersections as well as a representation of the detected fiducial locations. The oblique slice may allow the user to assess the virtual model matching to detected fiducial locations in the third dimension of the image. User manipulation of the detected fiducial locations, such as, but not limited to, adding, moving, and/or deleting fiducials, may be possible on this oblique fiducial slice reconstruction which drives a re-registration of the virtual model with the fiducial locations.

Figure 4:
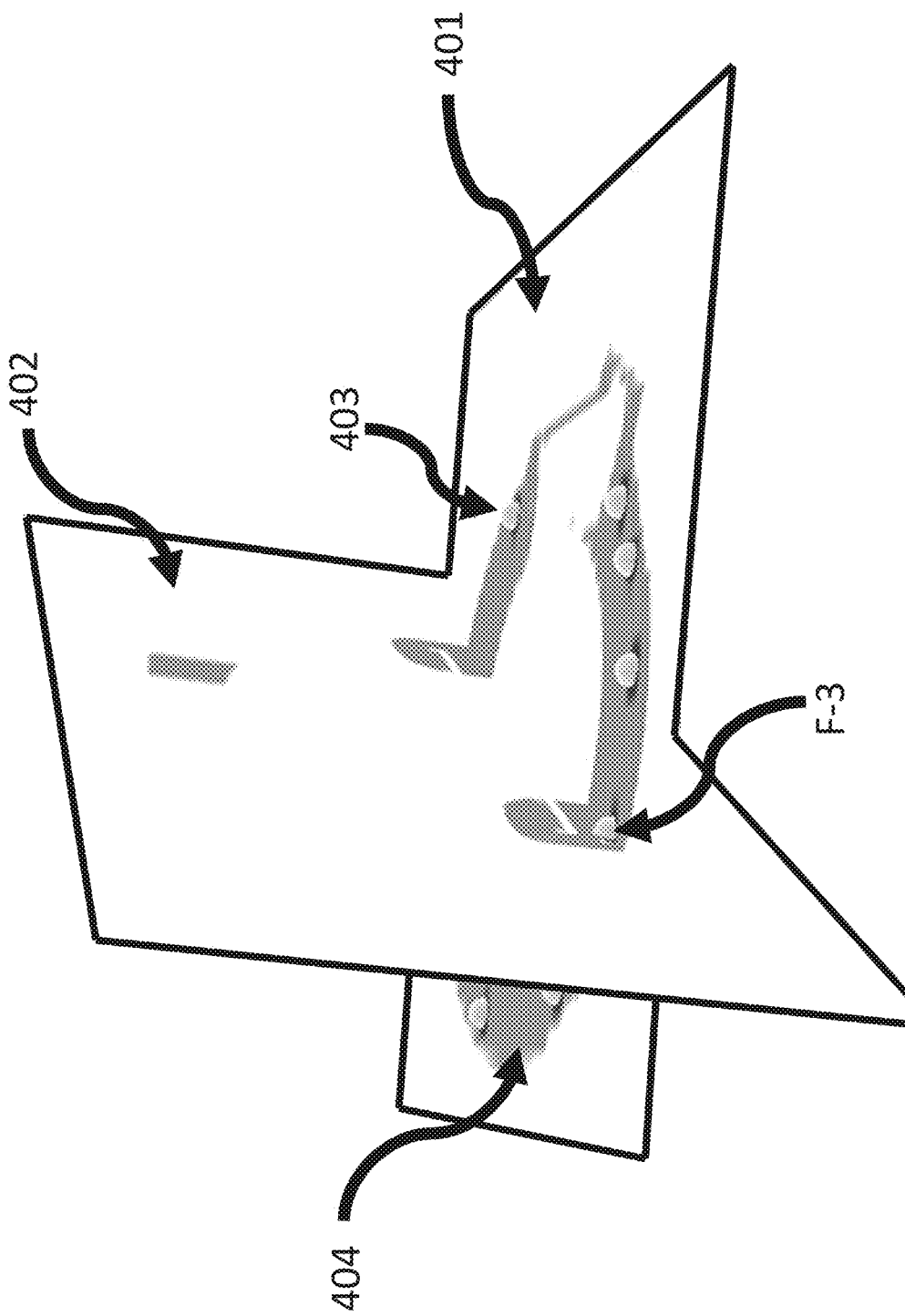
FIG. 4 illustrates at least one embodiment of a three dimensional (3D) representation of at least two multi-planar reconstructed planes for visualization of registration results in accordance with one or more aspects of the present disclosure.

In at least one embodiment of the multi-planar reconstructions as seen, for example, in FIG. 4, the subject image may be used to visualize the results of an automatic registration algorithm. The reconstructed device fiducial plane (e.g., from step S105) is represented by plane 401 as shown in FIG. 4. The reconstructed oblique slice (e.g., from step S106) for detected fiducial F-3 is depicted by slice 402. A three dimensional (3D) model of the template matched virtual fiducials is indicated by arrow 403, and is shown in relation to the imaged device (e.g., the guidance device 105) containing fiducials as indicated by arrow 404.

Figure 5:
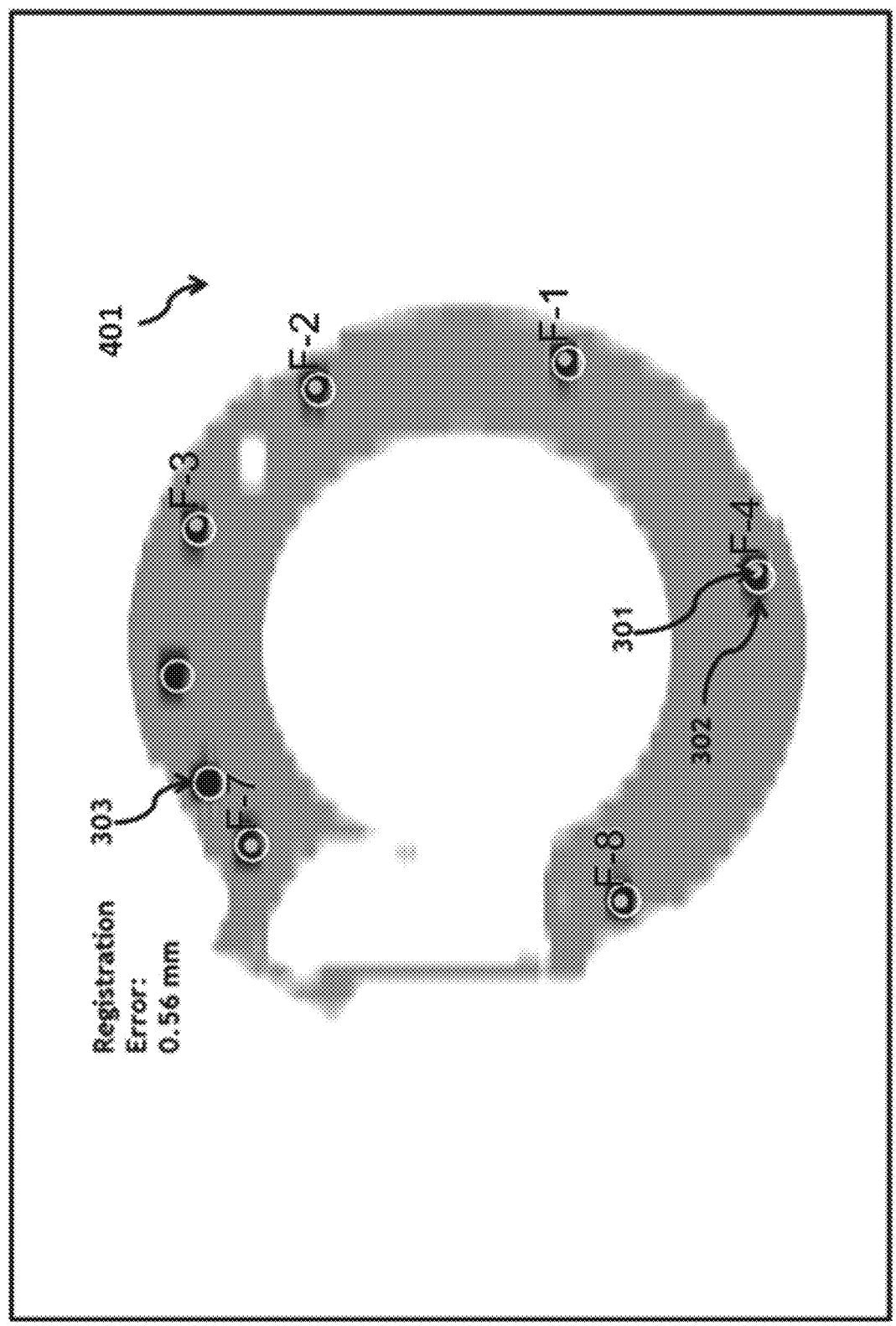
FIG. 5 is at least one embodiment of a multi-planar reconstruction of an automatic registration algorithm detected device fiducial plane with overlaid detected fiducial locations 301 and overlaid slice intersections of the virtual fiducial model 302 in accordance with one or more aspects of the present disclosure.

At least another embodiment of a multi-planar reconstruction of the automatic registration algorithm detected fiducial plane (e.g., from step S105; see e.g., the plane 401) is shown in FIG. 5. The multi-planar reconstruction has overlays that depict the registration algorithm detected fiducial locations (e.g., obtained via step S106) by image feature 301. In this embodiment, the detected fiducial locations are represented as a dot, for example; in one or more embodiments, the detected fiducial locations may be represented by any other indicator, such as, but not limited to, boxes, triangles, squares, or any other shape or marker. The multi-planar reconstruction, in at least the subject embodiment, also features overlays that depict the slice intersection of the virtual fiducial model (see step S107) by image feature 302. In at least this embodiment, the slice intersections of the virtual model fiducials are represented as an outline of the fiducial model. In one or more embodiments, the slice intersections may be represented by other indicators (e.g., outlines corresponding to other shapes and sizes, dashed marks, different colors, or other indicators, etc.). This embodiment illustrates the intuitive nature of this image presentation of automatic registration results. The user is able to quickly and clearly visualize all fiducial markers, analyze the detected fiducial locations, realize undetected fiducials depicted, for example, by indicator 303, and correlate with the overall registration error, which may be, for example, shown in the upper left corner (or any other available location) of the image, in this example. The user may then manually correct registration by moving any of the detected fiducial locations, adding undetected fiducials, and/or deleting misdetected fiducials leading to an auto recalculation of the template matching between fiducials detected in the medical images and the virtual model of the fiducials, and thus the registration error. Visually the user may quickly and easily match the virtual device model to the high intensity fiducials (e.g., F-1 through F-8, F-1, F-2, F-3, F-4, F-7, F-8, fiducial markers 209, etc.) in the images.

In at least one or more embodiments, on the fly (e.g., when needed, in real time, manual, automatic, during a medical procedure, while in progress, etc.) update(s) of template matching and registration error calculations based on user manipulation of detected fiducial locations (e.g., such as, but not limited to, adding, deleting, and/or moving fiducial locations) may be provided. As such, a user may receive, or be provided with, immediate feedback on how the user manipulation of detected fiducial locations affects the registration, and/or affects the matching of the virtual model and imaged fiducials (aka template matching), providing an intuitive method for the user to optimize the registration.

Figure 6:
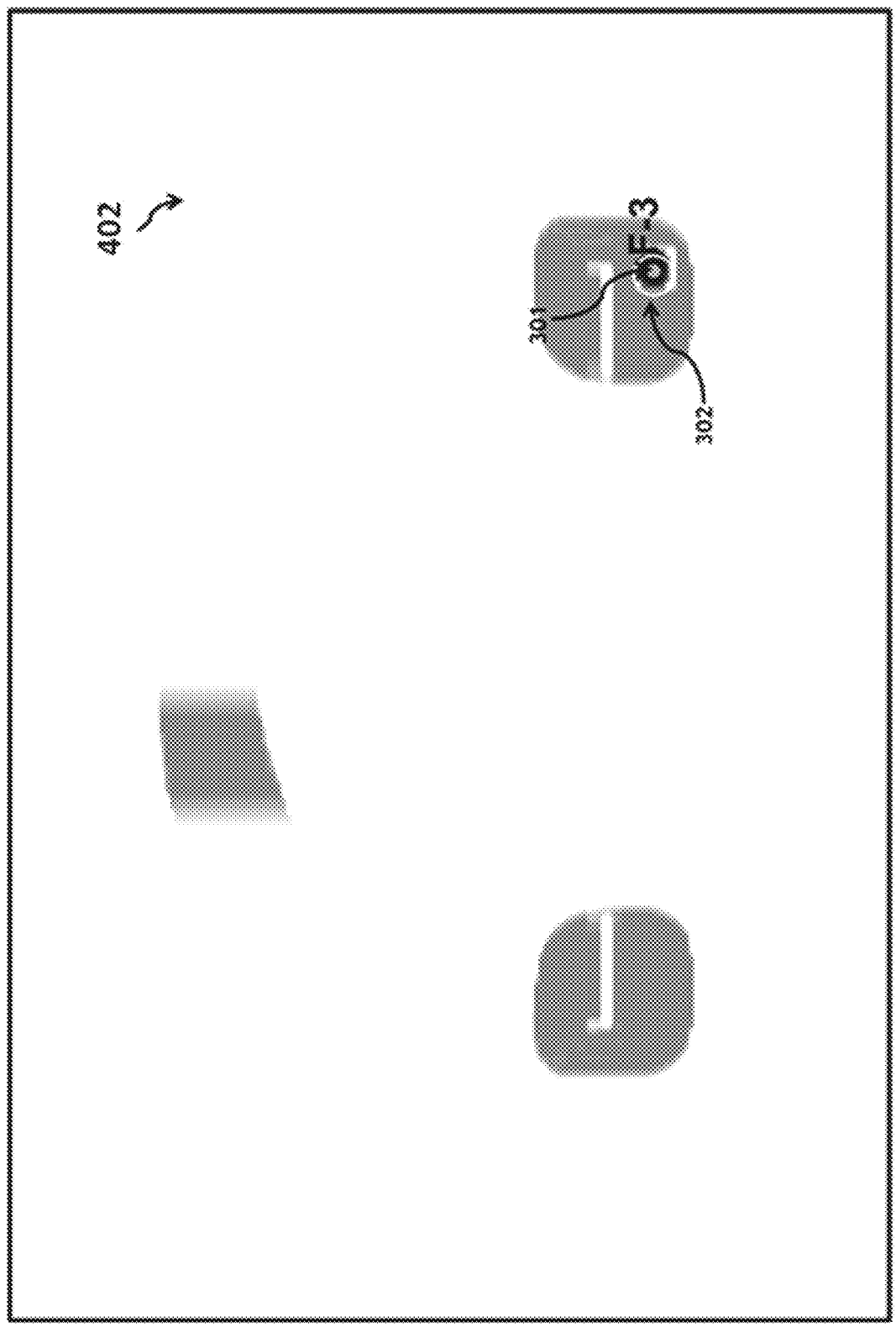
FIG. 6 is a depiction of at least one embodiment of a multi-planar reconstruction of an oblique slice reconstruction of an automatic registration algorithm detected fiducial marker in accordance with one or more aspects of the present disclosure.

At least a further embodiment of multi-planar reconstruction of an oblique fiducial slice (see step S108; see also, oblique slice 402) is shown in FIG. 6. The multi-planar reconstruction has overlays that depict the detected fiducial location(s) (see step S106) by the image feature 301. In at least this embodiment, the detected fiducial location(s) is/are represented as a dot or dots, for example; in one or more embodiments, the detected fiducial locations may be represented by any other indicator, such as, but not limited to, boxes, triangles, squares, or any other shape or marker. The multi-planar reconstruction also features overlays that depict the slice intersection of the virtual fiducial model (see step S107) by the image feature 302. In this embodiment, the slice intersections of the virtual model fiducials are represented as an outline of the fiducial. In one or more embodiments, the slice intersections may be represented by other indicators (e.g., outlines corresponding to other shapes and sizes, dashed marks, different colors, or other indicators, etc.). At least the embodiment shown in FIG. 5 and described above allows for fiducial location adjustment in at least two dimensions, and this reconstructed oblique slice shown in FIG. 6 provides the ability to adjust fiducial location in the 3$^{rd}$ dimension. For example, the user can click and drag the fiducial location in either the fiducial plane reconstruction depicted in the embodiment of FIG. 5 giving 2 degrees of freedom or in the oblique slice reconstruction depicted in this embodiment shown in FIG. 6, which provides the 3$^{rd}$ degree of freedom. This intuitive presentation of the registration results allows the user to quickly fine tune registration, which makes the registration process quicker and less burdensome to the user.

Structure of the guidance device 105 may incorporate one or more features as discussed in U.S. Provisional Patent Application No. 62/764,849, filed on Aug. 15, 2018, which is incorporated by reference herein in its entirety, and as discussed in U.S. Provisional Patent Application No. 62/875,243, as discussed in U.S. Provisional Patent App. No. 62/764,820, and/or as discussed in U.S. patent application Ser. No. 16/539,769, the applications of which are incorporated by reference herein in their entireties. For example, the fixed portion 205 and the moveable portion 206 may operate using a bearing. The bearing may be a ball bearing or any other suitable bearing structure known in the art that allows for relative motion between two concentric rings or similarly sized and/or shaped mating portions of the device or system 105. For example, the bearing may be a plain bearing, a roller bearing, and the like. The fixed portion 205 may further include a seal, which protects the bearing by preventing contamination from the external environment from coming into contact with the bearing. In one or more embodiments, the fixed portion 205 may further include a grip. The grip may be attached to or integral with the fixed portion 205. The grip provides a mechanism for the operator to increase stability of the fixed portion 205 during insertion of the medical instrument. Additionally, the grip may house electronic components relating to the use of LED arrays, which are used to indicate information to the user. The grip may also include visible markers for the medical images. In one or more embodiments, the fixed portion 205 and/or the movable portion 206 may include a gap that operates as an interruption to permit a medical instrument to pass through the gap and into the opening of the guidance device 105. The medical instrument can be an ablation probe in cryoablation, microwave ablation, radiofrequency ablation, laser ablation and irreversible electroporation ablation. Also, the medical instrument can be a needle-like device, for example a biopsy needle, an aspiration needle and a drainage needle. The gap may include the width wide enough to get the medical instrument through for releasing/accepting.

The arc member 207 has an arc shape that spans an angle relative to the horizontal plane (see e.g., FIGS. 1 and 2B). The angle 170 may be from 60 to 170 degrees, more preferably 120 to 150 degrees. The angle may be from 0 to 180 degrees in one or more embodiments. The arc member 207, as aforementioned, may include a guide surface that provides a guidance area for the instrument. The arc member 207 may include a plurality of angular reference marks on the guide surface (as shown, for example, in FIG. 1). The surface of the arc member 207 may have a different color than the color of the surface on the opposite side of the arc member 207. Having a different color allows the operator to quickly and easily ascertain which surface is the guide surface. This is particularly useful in an embodiment which lacks the plurality of reference marks. The angular reference marks signify an angle around a center point of the opening of the guidance device 105.

The angular reference marks may be visible optically as well as in CT and X-ray images utilizing radio-opaque material. The radio-opaque material may be, but is not limited to, plastic including fillers of barium sulfate, bismuth subcarbonate, bismuth oxychloride, tungsten, etc. The arc member 207 may have a thickness. The thickness may be $\frac{1}{15}$ to $\frac{1}{3}$ the diameter of the opening of the guidance device 105, more preferably $\frac{1}{12}$ to $\frac{1}{5}$ the diameter of the opening, more preferably $\frac{1}{10}$ to $\frac{1}{5}$ the diameter of the opening. In various embodiments, the angular reference marks may be provided on the thickness portion of the arc member 207, thus allowing for viewing of the angle from a top perspective. The angular reference marks may be envisaged in any desired increment and/or scale, with various increments being sized differently for indication purposes.

The ends of the arc member 207 may be integrally formed with the frame of the moveable portion 206 such that the entire upper or first portion (e.g., the moveable portion 206 and the arc member 207) of the device 105 and/or the device 105 is monolithically formed. That is, the entire upper or first portion (e.g., the moveable portion 206 and the arc member 207) of the device and/or the device 105 may be cast as a single piece of material. Alternatively, as shown in FIG. 2B, the arc portion or member 207 may include the hinge assembly 62, 64 and the locking mechanism 80 as discussed above.

In some embodiments, the plurality of angular reference marks on the guide surface of the arc member 207 may comprise LED indicators. These LED indicators provide illumination of the guide surface or they may be turned on to indicate, for example, an angle of planned entry (e.g., a lit indicator appears at the planned entry angle). For a medical guidance apparatus that is configured to detect the angle of a needle positioned in or near the medical guidance apparatus, the LEDs may be used to display when the needle is approaching or at a 'correct angle' by, for example, signaling with a green light at that angle.

Each of the monolithic structure of the first or upper portion (e.g., the moveable portion 206 and the arc member 207), the device 105, etc. contributes to one or more structural advantages. For example, when force is applied to the arc member 207 in a direction against the guide surface of the arc member 207, one or more of these structural features provide sufficient stiffness and rigidity to provide support and to minimize deflection, thereby providing sufficient support to the user when position an instrument. This structure provides a high rigidity while the structure still provides an opening for needle egress. This is in contrast to a cantilever shape, i.e., an open frame. The monolithic structure has a greater stiffness and may withstand the forces associated with needle placement and maneuvering with smaller deflection.

Additionally, because of the monolithic structure(s), assembly error may be avoided in one or more embodiments. The structure of the guidance device 105 and/or the upper or first portion (e.g., the moveable portion 206 and the arc member 207) is able to provide this structural support despite having the aforementioned gap in one or more embodiments.

As noted above the upper or first portion (e.g., the moveable portion 206 and the arc member 207) of the guidance device 105 may be rotatably coupled with the fixed portion 205. In one aspect, this may be achieved by mechanically coupling the frame of the upper or first portion (e.g., the moveable portion 206 and the arc member 207) of the guidance device 105 to the moveable portion 206 via a mechanical interface as discussed in U.S. Provisional Patent Application No. 62/764,849, filed on Aug. 15, 2018, the entirety of which is incorporated by reference herein, and/or as discussed in U.S. Provisional Patent Application No. 62/764,849, as discussed in U.S. Provisional Patent Application No. 62/875,243, as discussed in U.S. Provisional Patent App. No. 62/764,820, and/or as discussed in U.S. patent application Ser. No. 16/539,769, the applications of which are incorporated by reference herein in their entireties. The mechanical components may be any suitable mating structure such as corresponding male/female components, snap fitting, bayonet mount and Velcro-style fastener, and the like.

Once the upper or first portion (e.g., the moveable portion 206 and the arc member 207) of the guidance device 105 is mated with base assembly no via the moveable portion 206, the upper or first portion (e.g., the moveable portion 206 and the arc member 207) of the guidance device 105 is able to freely rotate via the moveable portion 206. That is, the moveable portion 206 being rotatable about an axis relative to the stationary fixed portion 205 (as described above), and the upper or first portion (e.g., the moveable portion 206 and the arc member 207) of the guidance device 105 being coupled with the moveable portion 206, allows the upper or first portion (e.g., the moveable portion 206 and the arc member 207) of the guidance device 105 and the moveable portion 206 to rotate together about the axis when a rotational force is applied to either the moveable portion 206 or the upper or first portion (e.g., the moveable portion 206 and the arc member 207, a part of the arc member 207, etc.) of the guidance device 105.

In one or more embodiments, the guide or moveable portion 206 may be attached to an arc member 207, as shown in FIG. 2B, comprising a rail and an instrument holder 70. The arc member 207 may define the rail along which the instrument holder 70 may slide. The instrument holder 70 may be in the shape of a half cylindrical groove sized to receive an instrument, for example a needle (see e.g., the needle 300). The instrument holder 70 may be shaped to fit other instruments, depending on the procedure being conducted. The instrument holder 70 may provide constrained guidance for the instrument, such as the needle (e.g., the needle 300). The instrument holder 70 may accurately guide the instrument, such as the needle (e.g., the needle 300), by directing the half cylindrical groove to the target trajectory. Thus, the instrument holder 70 may increase accuracy and may reduce intervention.

The instrument holder 70 may be shaped to fit multiple instruments in a pre-set geometric configuration, for example multiple cryo-ablation needles arranged so the two or more needles will be held by the instrument holder 70. For example, two needles may be held simultaneously, both positioned near the arc member 207 or tangential to the arc member 207. In other examples, three, four, or more needles may be held simultaneously by the instrument holder 70 in a triangle, square, diamond, etc. configuration. The instrument holder 70 may provide constrained guidance for the instruments to maintain the geometric relationship between instruments (e.g., parallel insertion) during the procedure.

Another optional feature of some embodiments is a differentiating marker located on the guide or the movable portion 206. The differentiating marker is shown as a different color or hue located on the surfaces of the guide or movable portion 206 visible during use. This differentiates the portion of the medical guidance apparatus, device or system where the needle will be placed and guided. The differentiating marker may be, for example, a different color, an adhesive, a pattern, or some other differentiator that the physician or clinician can use to quickly differentiate which portion of the device should be used during needle placement.

In accordance with at least one aspect of the present disclosure and as aforementioned, one or more methods for performing needle guidance planning and/or performance and one or more methods for visualizing and manipulating registration results are provided herein. At least FIGS. 8-13 illustrate flow charts of at least one respective embodiment of a method for performing needle guidance and/or performance using a guidance device (e.g., such as a device 105 as shown in FIG. 7), system (e.g., such as a system 10 as shown in FIG. 7) or storage medium. At least one embodiment of a system 10 may include a medical device (e.g., an ablation device, a biopsy device, etc.) 1, a needle guidance planning and/or performance computing system (which may include software and/or hardware for implementing the needle guidance planning and/or performance) or computer/processor 2 (alternative embodiment of a computer 2' that may be used is discussed herein below), a guidance device (such as, but not limited to, an image-plane localizer) 105, a Picture Archiving and communication system (PACS) 4 and an image scanner 5 (such as, but not limited to, a CT scanner, MRI device or other scanning apparatus). As shown diagrammatically in FIG. 7, the needle guidance planning and/or performance methods and/or visualization and manipulation of registration result(s) methods of the present disclosure may be involved with all major aspects of guidance planning and performance, including guiding one or more needles or other medical devices. For example, the system 2 may communicate with the image scanner 5 to request information for use in the guidance planning and/or performance, such as, but not limited to, bed or slice positions, and the image scanner 5 may send the requested information along with the images to the system 2 once a clinician uses the image scanner 5 to obtain the information via scans of the patient. By way of another example, the system 2 may communicate (wirelessly or in a wired configuration) and be used with a guidance device (also referred to as a locator device) 105 (such as an image-plane localizer that may be a patient-mount device and may be rotated as shown to help locate to biological object, such as a lesion or tumor; the aforementioned embodiments shown in FIGS. 1-6 may also be employed in the system 2 as the guidance device) to obtain information from the patient when conducting needle guidance planning and/or performance. The system 2 may further communicate with a PACS 4 to send and receive images of a patient to facilitate and aid in the needle guidance planning and/or performance. Once the plan is formed, a clinician may use the system 2 along with a medical device (e.g., an ablation device, a biopsy device, etc.) 1 to consult a chart or plan (e.g., for needle guidance, for ablation, for biopsy, for a medical procedure, etc.) to understand the shape and/or size of the targeted biological object to undergo the medical procedure (e.g., ablation, biopsy, etc.). Each of the medical device 1, the system 2, the guidance device 105, the PACS 4 and the scanning device 5 may communicate in any way known to those skilled in the art, including, but not limited to, directly (via a communication network) or indirectly (via one or more of the other devices 1, 105 or 5; via one or more of the PACS 4 and the system 2; via clinician interaction; etc.). In one or more embodiments as discussed herein, the guidance device 105 may communicate wirelessly with one or more of the following: the medical device 1, the system 2, the PACS 4, and the scanning device 5. Preferably, in one or more embodiments, the guidance device 105 communicates wirelessly or in a wired connection with at least the system 2 or any other processor operating to interact with the guidance device 105 to perform the guidance planning and/or performance and/or the visualization and manipulation of registration result(s).

One or more embodiments of the guidance planning and performance and/or the visualization and manipulation of registration result(s) apparatuses and systems, and methods and storage mediums may operate to improve the determination of the needle or probe (and/or other medical device) trajectory. One or more embodiments of the present disclosure operate to reduce the number of scans, and consequently reduce the insertion and trajectory determination time. One or more embodiments greatly assist clinicians, including during the stages of determining insertion point, determining trajectory, performing initial probe insertion and performing full probe insertion, by providing a probe tracking and guidance system for faster execution of the medical procedure and needle guidance plan and better accuracy in positioning a probe or other medical device. The tracking and guidance system not only tracks the probe, needle, guidance device, and/or other medical device position and orientation, but also provides cues for visualization software with the target biological object (e.g., a patient's lesion, a patient's tumor, etc.) and critical structures from an IR's or other clinician's point of view. This visualization may be updated in real time to account for motion due to respiration and tissue deformation. The tracking and guidance system can also give IR the ability to define the trajectory and insert the probe remotely through a robotic device placed on the body of the patient or situated near the patient, controlling the probe from outside of the imaging (CT for example) suite. The remotely controlled operating system may shorten procedures by reducing the time moving in and out of the CT suite and mitigating the exposure to radiation.

In one or more embodiments, multi-probe or multi-needle guidance may be used in combination with any feature disclosed herein, including, but not limited to, guidance of the one or more needles or one or more probes (including wireless guidance thereof), with a margin map, with a medial axis or center line, with a security or credential check, etc. In one or more embodiments, the size and shape of a biological object, such as a lesion or tumor, may be used to determine whether two or more needles, and two or more probes/balloons, are needed to appropriately perform a medical procedure on the target area of the biological object (e.g., ablate a target ablation zone). In one or more embodiments, clinicians may employ a spherical balloon(s) for an ablation zone because it is easy to control. In one or more embodiments, the balloon or balloons may have a different shape, e.g., elliptical or other predetermined shape. Additionally or alternatively, the type of balloon and number of balloons/needles may vary depending on the type of ablation being performed. For example, when performing microwave ablation, RF ablation, laser ablation and/or cryoablation, a spherical balloon may be used or the ablation may require a shape other than spherical. Multi-probe or multi-needle procedures are useful. For example, ablation may be performed with two needles and multiple balloons to ablate a target ablation zone for a biological object, such as a tumor or lesion. The methods disclosed herein may be used to simulate or perform guidance planning when evaluating a biological object or a target/target zone and determining whether to use a two-needle (or more) insertion for a desired medical procedure (e.g., ablation, biopsy, etc.).

Preferably the image scanner 5 (best seen in FIGS. 7 and 8) (e.g., a CT scanner) operates to generate one or more images from scanning a patient body (or portion thereof) with and/or without the use of the guidance device 105.

At least a first processor (e.g., a processor or CPU 1201 of the system 2 shown in FIG. 7, the first processor 1201 of FIG. 8, a processor or CPU 1201 in a device as shown in system 2 of FIG. 13, a processor or CPU 1201 as shown in system 2 of FIG. 14, a processor or CPU 1201 in another device, etc.) operates to load scanned images (e.g., from the PACS 4 generally as aforementioned because scanned images may be stored in the PACS 4). In one or more embodiments, the first processor 1201 operates to load images from the image scanner 5 and/or from the PACS 4. The first processor 1201 preferably supports users (e.g., physicians, clinicians, etc.) to plan and/or perform needle or medical device guidance trajectories (which may include or involve one or more of insertion angle(s), depth(s), region(s)

of target(s) or interest(s), ablation power and duration if users use ablation needles, etc.). In one or more embodiments, the first processor 1201 may register scanned images and the guidance device 105 to calculate parameter(s) of one or more trajectories, fiducial locations, etc. In one or more embodiments, the first processor may read position information from an encoder (e.g., the encoder sensor 203) through a wired or wireless connection.

The first processor 1201 may detect fiducial markers (e.g., the aforementioned fiducial markers 209, F-1 through F-8, any of F-1 through F-8, etc.) from images (e.g., CT images) automatically or may detect fiducial markers via manual user interaction. As aforementioned, detection of fiducial markers may not be needed when the guidance device 105 is placed on a designated or predefined position. In one or more embodiments, the first processor 1201 may operate to reconstruct oblique image(s) (although this is an optional feature that may not be used, for example, in a case where the system (e.g., the system 2) does not show reconstructed oblique images on a display (e.g., the display 1209 of FIG. 8, the display of FIG. 7, the display or screen 1209 of FIG. 13, etc.). The first processor 1201 may allow users to compare pre-procedure images and post-procedure images (e.g., images taken before and after ablation).

Figure 8:
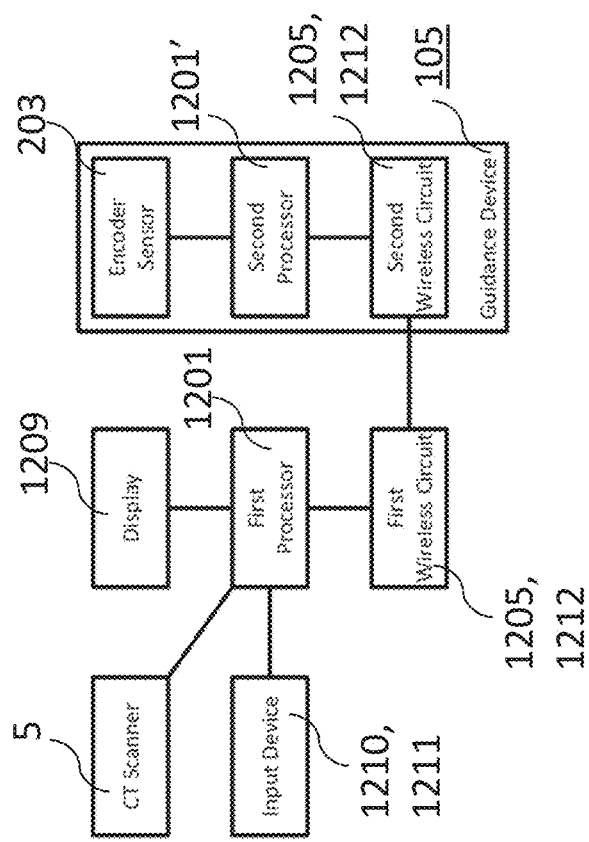
FIG. 8 is a schematic diagram of at least one embodiment of a communication signal and/or electrical connection(s) between a first processor and a second processor of a guidance device and/or system in accordance with one or more aspects of the present disclosure.
Figure 13:
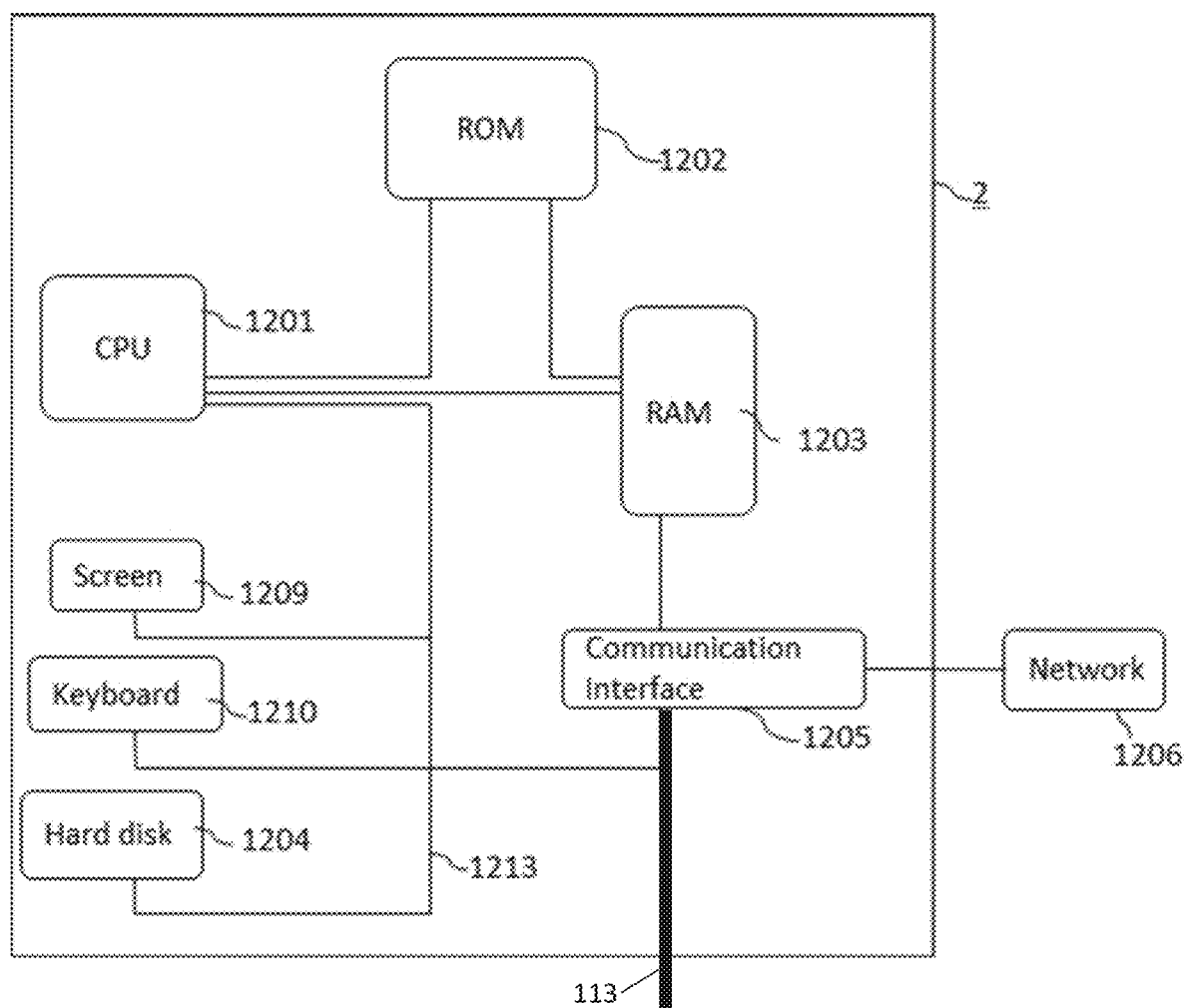
FIG. 13 shows a schematic diagram of an embodiment of a computer or processor that may be used with one or more embodiments of a needle guidance and/or performance method, apparatus or system in accordance with one or more aspects of the present disclosure.
Figure 14:
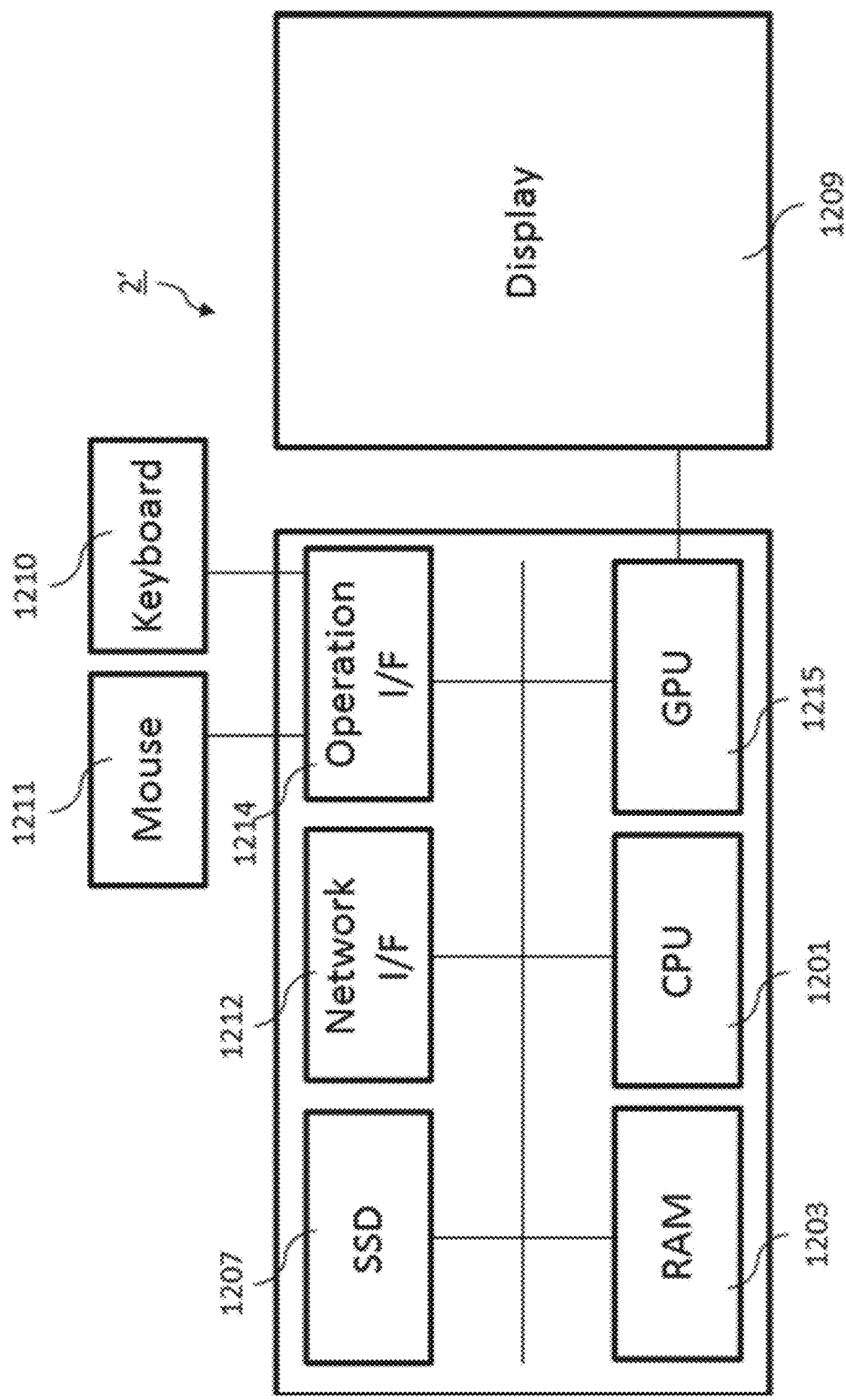
FIG. 14 shows a schematic diagram of another embodiment of a processor or computer that may be used with one or more embodiments of a needle guidance and/or performance method, apparatus or system in accordance with one or more aspects of the present disclosure.

A display (e.g., the display 1209 of FIG. 8, the display of FIG. 7, the display 1209 of FIG. 13, etc.) is preferably used in one or more embodiments to enable user interaction with an input device (e.g., a keyboard 1210 and/or a mouse 1211 as best seen in FIGS. 8 and 13-14). The display (e.g., the display 1209) may operate to do at least one or more of the following: show scanned images (e.g., CT images), show status (e.g., of the patient, procedure, one or more needles, etc.), visualize trajectories, compare pre-procedure and post-procedure images, etc.

Preferably, the first processor 1201 is connected to, and/or communicates with, a first wireless circuit (e.g., first wireless circuit 1205, 1212 as shown in FIG. 8, communication interface 1205 as shown in FIG. 13, network interface as shown in FIG. 14 (which may operate as a wired and/or wireless communication circuit), etc.) to enable communication between the first processor 1201 and at least a second processor (e.g., the second processor 1201' of the guidance device 105 as shown in FIG. 8, a processor of the system 2 or the system 2' as best seen in FIGS. 7 and 13-14, etc.).

Preferably, the second processor (also referred to herein as "the Second Processor") 1201' is connected to, and/or communicates with, a second wireless circuit (e.g., second wireless circuit 1205, 1212 as shown in FIG. 8, communication interface 1205 as shown in FIG. 13, network interface as shown in FIG. 14 (which may operate as a wired and/or wireless communication circuit), etc.) to enable communication between the first processor 1201 and the second processor 1201' to transfer information therebetween. In one or more embodiments, the second processor 1201' operates to do one or more of the following: read one or more positions from an encoder (e.g., the encoder sensor 203, the encoder sensor 203 based on interaction with the encoder scale 204, etc.); detect one or more errors of an encoder (e.g., the encoder sensor 203, the encoder sensor 203 based on interaction with the encoder scale 204, etc.) and/or the second processor 1201'; and control LEDs (see aforementioned discussion regarding LEDs, including, but not limited to, the LEDs 210 of FIG. 1, etc.).

In one or more embodiments, the guidance device 105 includes at least three LEDs to convey information to a user of the device 105. A center or middle LED may operate to indicate status information of the device 105 and/or the guidance status, and two other LEDs may indicate rotational direction for guidance. Various combinations of indicational patterns may be used for the LEDs. For example, in at least one embodiment, in a case where the center or middle LED is flashing, then the LED is indicating that an error occurred. In a case where the center or middle LED is "On", then one or more guidance features are enabled. In a case where the center or middle LED is "Off", then the one or more guidance features are disabled. In one or more embodiments, when one of the other two rotational direction LEDs is flashing, then that indicates guidance is occurring and that the user should change the insertion angle in one direction. In one or more embodiments, when a second of the other two rotational direction LEDs is flashing, then that indicates guidance is occurring and that the user should change the insertion angle in a second direction. When both of the two rotational direction LEDs are on, then the one or more guidance features are enabled, and the user should stop adjusting the insertion angle. When both of the two rotational direction LEDs are off, then the one or more guidance features are disabled. In one or more embodiments, a frequency of the flashing of one or more of the LEDs may be used, and may change depending on distance (angle) between a current position and a target position. For example, in at least one embodiment, when a distance (angle) is long, the frequency may be low, and when the distance (angle) is near/short, then the frequency may be high. Other modifications to the number of LEDs, frequency of the flashing, information conveyed via the LEDs and configuration of the LEDs may be made depending on the information that a user desires to receive from the device 105 (and construction of the device 105 may occur based on such specifications). The LEDs 210 may also be used to indicate whether the fiducial location is accurate or not, and may indicate to a user which way to move, guide or rotate the guidance device 105 to achieve accurate registration of the guidance device 105.

In one or more embodiments, the information transferred between the first processor 1201 and the second processor 1201' includes one or more of the following: a position detected from an encoder (e.g., the encoder sensor 203 as aforementioned; in one or more embodiments, the detected position may be an angle position), a status of an encoder (e.g., the encoder sensor 203), a status of the second processor 1201', a status of the first processor 1201, a target position based on a trajectory or trajectories, a status of the guidance device 105, and a signal to enable or disable one or more guidance features of the guidance device 105. In one or more embodiments, an enable signal for the guidance device 105 may not be needed in a case where reception of target position information enables the one guidance features, and, in one or more embodiments, a disable signal for the guidance device 105 may not be needed in a case where the second processor 1201' stops the one or more guidance features automatically. In one or more embodiments, the signal to enable or disable one or more guidance features may include a guidance completion signal or information to be transferred between the first processor 1201 and the second processor 1201'.

Additionally, information conveyed by one or more components, such as, but not limited to, one or more of the device 105, the computer 2, the system 10, the first and second processors 1201, 1201', etc., may depend on the desired specifications for the guidance device and/or system. For example, structural attributes (defining how such components are structurally built to achieve the desired functional behavior) may change depending on a desired medical procedure. For example, in one or more embodiments, the guidance device 105, the system to and/or one or more other components of the system to may be used for the medical procedure of ablating tumors in a patient body. Because tumors may be invisible, users may confirm where tumors are using the image scanner 5 (e.g., a CT scanner) or other scan devices. The computer 2, the guidance device 105, and/or the guidance system to calculates an insertion point, an insertion angle, a depth, an ablation time and an ablation power of candidate trajectories, and users of the system to may input such calculated results into the system to for needle guidance planning and/or performance and/or for visualization and manipulation of registration result(s). After a trajectory users choose is set to the guidance device 105, users may insert the needle 300 (best seen in FIG. 1; e.g., the needle may be for ablation in an ablation procedure, a biopsy procedure, etc.) with the guidance device 105 accurately.

In one or more embodiments, users may turn on the whole guidance system 10 including the guidance device 105 at first. The guidance system to may establish a wireless connection between the first wireless circuit 1205, 1212 and the second wireless circuit 1205, 1212 in a startup routine. Additionally or alternatively, a wired connection may be used.

After the preparation or the startup routine, a patient may be scanned by the image scanner 5 (e.g., the CT scanner 5 as shown in FIG. 8) with, or using, a disposable grid in one or more embodiments. The disposable grid operates to allow users find an insertion point more easily and more accurately. A disposable grid known to those skilled in the art may be used (such as, but not limited to, a Beekley Medical® Guidelines® CT Biopsy Grid 217, which may be obtained via Beekley Medical's website: https://www.beekley.com/Product-Details/GuideLines/CT-Biopsy-Grid-217). In one or more embodiments, users may use disposable fiducial markers (such as the aforementioned fiducial markers 209, fiducials F-1 through F-8, any of F-1 through F-8, etc.) instead of a disposable grid. Additionally or alternatively, users may find the insertion point without the grid and/or fiducial markers 209, F-1 through F-8, etc.

As aforementioned, in one or more embodiments, the first processor 1201 may load the scanned images, and may show the scanned images on the display 1209. A user or users of the system 10 may find a target region or regions from the scanned images and may set the target region or regions to the guidance system 10. The user or users may input data via one or more input devices (e.g., the keyboard 1210, the mouse 1211, etc.). Once settings and/or data are input, the first processor 1201 may then commence interaction for the needle guidance planning and/or performance.

After a user or users define an insertion point and make a trajectory, then the one or more users may put the guidance device 105 on or around the insertion point of the patient. The guidance device 105 may be fixed to the patient using any known methods or tools to those skilled in the art, including, but not limited to, using sticky tape. Thereafter, the patient may be scanned by the image scanner 5 (e.g., a CT scanner) with the guidance device 105 in place on the patient, and the registration result(s) may be determined and manipulated as needed to achieve accurate registration of the guidance device 105.

In one or more embodiments, at least the first processor 1201 registers the guidance device 105 and the scanned images using the fiducial markers 209, F-1 through F-8, any of F-1 through F-8, etc. The first processor 1201 is able to detect a position of the guidance device 105 in 3D space because the fiducial markers 209, F-1 through F-8, any of F-1 through F-8, etc. are placed in the fixed part or portion 205 of guidance device 105 (see e.g., FIGS. 2A and 4-6). Alternatively or additionally, registration may be performed using the other structural configurations and/or methods discussed herein, or may be set by using data defining a predetermined location/position as aforementioned.

After the guidance device 105 is registered, the first processor 1201 may update the trajectory automatically to reduce error (or a user may update the trajectory manually via interaction with the first processor 1201 when desired). To avoid errors that may occur in a situation where a center of the guidance device 105 is different from a predefined insertion point, in one or more embodiments, the first processor 1201 may update the insertion point to set the center of the guidance device 105, and may calculate the insertion angle and depth thereafter.

In one or more embodiments, the first processor 1201 may send insertion angle information, and may enable a signal of one or more guidance features to the guidance device 105 (e.g., before the guidance device 105 beings to guide the one or more needles and/or other medical apparatus attached thereto for guidance). After the one or more guidance features of the guidance device 105 are enabled, the LEDs or other indicators of the device 105 may be lit or turned on to indicate information for the user or users. The guidance device 105 may begin guidance when target angle information is received. Then, an enable or disable signal may not have to be used in one or more embodiments as aforementioned.

Additionally, in one or more embodiments, the first processor 1201 may reconstruct an oblique image based on loaded images and angle information. The first processor 1201 may show the image on the display 1209, and may update the displayed image to be synchronized with new angle information.

In a case where the medical procedure is ablation for example, the method(s) may include one or more ablation planning and performance steps, including, but not limited to, one or more of the following: (i) loading images (e.g., from a scanner, a PACS or other scanning device/system, or using a fresh or newly scanned image) (see step S1 in FIG. 9); (ii) visualizing images (e.g., such as by showing multiple panes (views, such as, but not limited to, axial, coronal, sagittal, 3 dimensional (3D), etc.) (e.g., each view may represent a different aspect of an image (e.g., a CT DICOM image); showing at least one pane of an image; loading an image (e.g., a CT DICOM image) and displaying it on a computer for visualization purposes; allowing a user to interact with a displayed image in one or more panes by moving at least one line (e.g., an axis or axes) to cut through one or more planes to reformat a 3D data set and display the reformatted slices in the 3D view; etc.)) (see step S2 in FIG. 9); (iii) identifying a treating zone or target (e.g., a lesion or tumor) (see step S3 in FIG. 9); (iv) defining a target point, an entry point and a trajectory between the target and entry points (see step S4 in FIG. 9) (as shown in step S4*b*, Step S4 may include repeating the process if there is one trajectory or there are multiple trajectories (and multiple target points) depending on a characteristic of a tumor or lesion); and (v) correspond the entry point in a particular image to an entry point for a body of the patient (see step S5 in FIG. 9). Determination of the target points (and the number of target points) may be at the discretion of the clinicians in one or more embodiments, or may be dependent upon the characteristic(s) of the target biological object, such as a lesion or tumor (e.g., a size of the lesion or tumor, a shape of the lesion or tumor, etc.). In one or more embodiments of the present disclosure, a method is provided to determine or suggest a target point or points that is clinically the best choice (e.g., mathematically, statistically, etc.) for placement of the target point(s). In one or more embodiments, target point(s) may be determined by finding or determining a medial axis or center line of the target or treating zone (see step S4 of FIG. 9).

Figure 9:
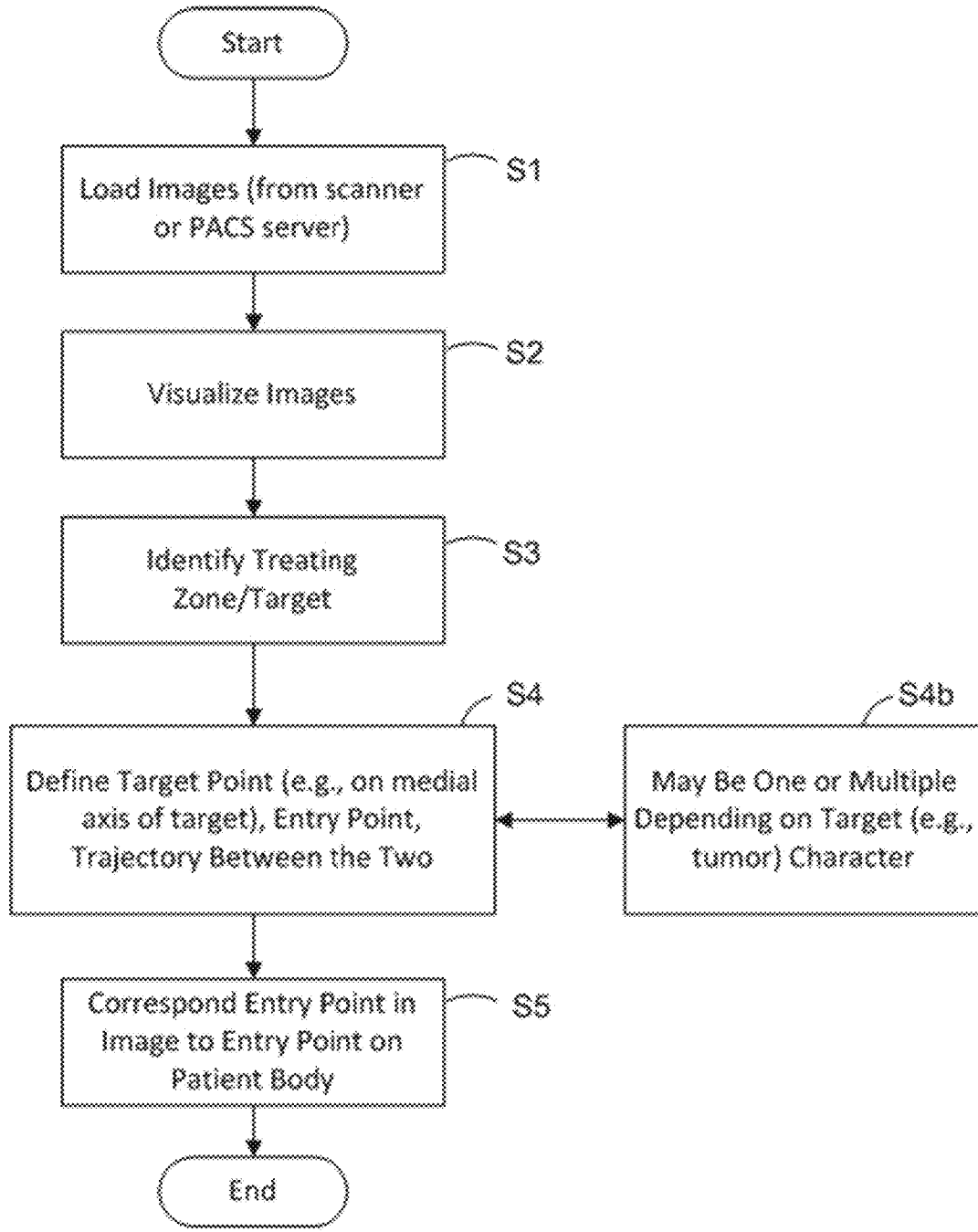
FIG. 9 is a flow chart showing at least one embodiment of a method for performing ablation and/or needle guidance planning and/or performance in accordance with one or more aspects of the present disclosure.
Figure 10:
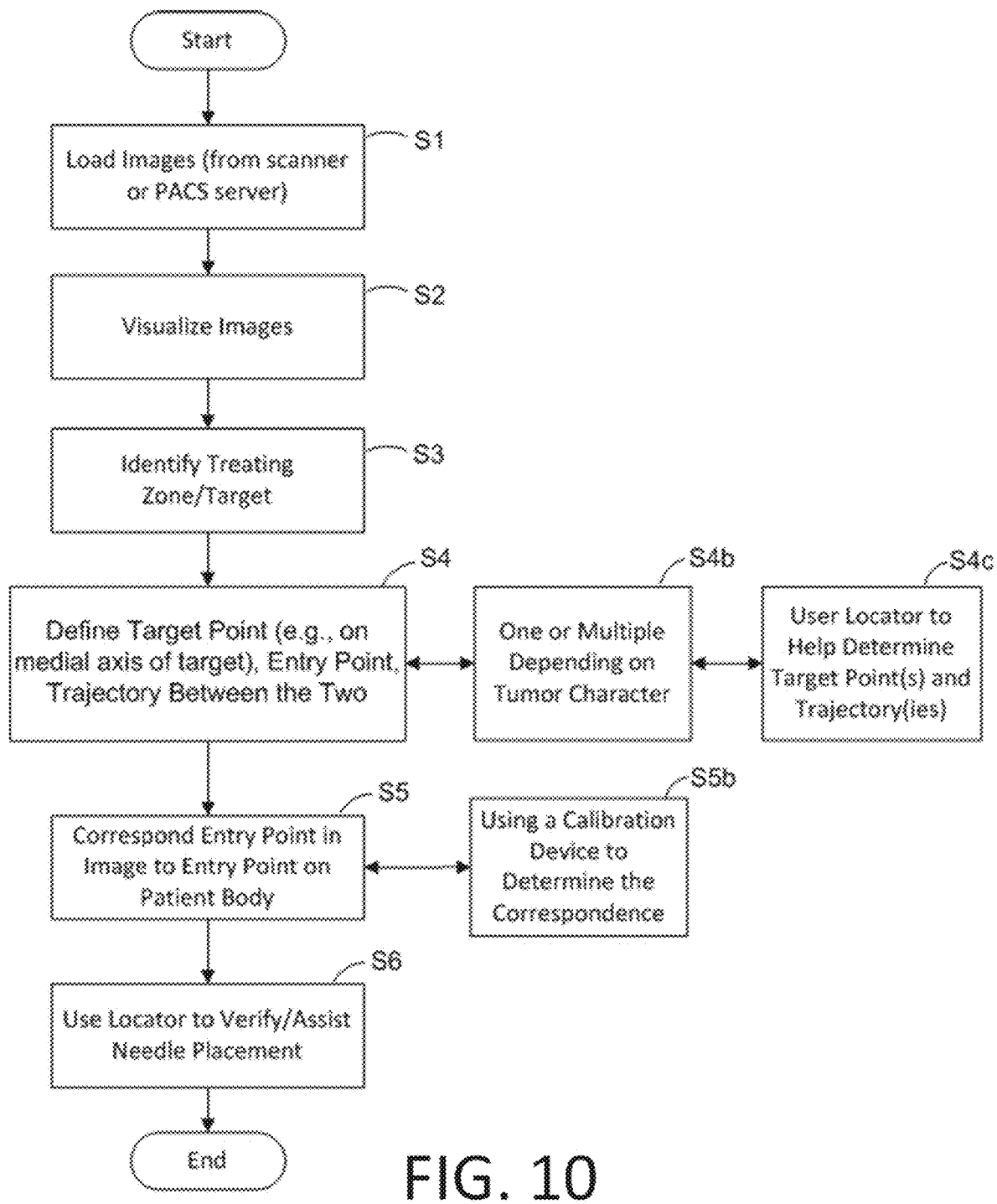
FIG. 10 is a flow chart showing at least another embodiment of a method for performing ablation and/or needle guidance planning and/or performance in accordance with one or more aspects of the present disclosure.

For any identification of a target or targets step(s) discussed herein (such as, but not limited to, step S3 of FIGS. 9-10; step(s) S4, S4b of FIG. 9; step(s) S4, S4b, 54c of FIG. to; etc.), any method of identifying a target biological object or zone, including those known to those skilled in the art, such as a clinician, and including the additional method(s) provided herein, may be employed. For example, in one or more embodiments, a target zone and target points are to be identified. A target zone may be identified by an image segmentation method(s). Clinicians may initially define a few points, called seeds, which may or may not be the target points within an identified a target region, such as a lesion or tumor region. In one or more embodiments, an active contour model, such as a snake algorithm (see e.g., one example explained by C. Xu and J. L. Prince in "Gradient Vector Flow: A New External Force for Snakes", Proc. IEEE Conf. on Comp. Vis. Patt. Recog. (CVPR), Los Alamitos: Comp. Soc. Press, pp. 66-71, June 1997), may be used to iteratively determine a boundary of the target region. The initial seeds may not converge to a true boundary quickly, so, in one or more embodiments, a watershed method (see e.g., one example explained by Gouze A., De Roover C., Herbulot A., Debreuve E., Barlaud M., Macq B. in "Watershed-driven Active Contours for Moving Object Segmentation", in Proceedings of IEEE International Conference on Image Processing (ICIP), vol. II, pp 818-821, Genova, Italie, September 2005) may be used together with the snake algorithm to make the segmentation smoother and faster. Compared to manually drawing a boundary of a target region, such as a lesion or tumor region, such a method or methods generate a far more accurate and consistent boundary, which may be used to determine a volume of a target (e.g., a tumor or lesion) and may be used in a later stage for quantitatively characterizing the tumor or lesion and assessing ablation results. The resulting boundary forms a target zone.

Additionally or alternatively, one or more method(s) of the present disclosure may further include performing ablation planning and/or performance with the guidance device 105 as shown in FIG. 7. In addition to the steps shown in FIG. 9 (the details of which are aforementioned and will not be repeated herein accordingly), such one or more method(s) employing a guidance device, such as the guidance device 105 may further include, but are not limited to, one or more of the following: (i) using a guidance device, such as the guidance device 105, to help determine the target point(s) and trajectory(ies) in steps S4 and/or S4b (see also steps S4, S4b and S4c in FIG. 10); (ii) using a calibration device (e.g., such as, but not limited to, fiducial markers (e.g., the fiducial markers 209, the fiducials F-1 through F-8, any of the fiducials F-1 through F-8, etc.), systems and methods of registration, such as those disclosed in U.S. patent application Ser. No. 14/755,654 and published in U.S. Pat. Pub. No. 2017/0000581, which are incorporated by reference herein in their entireties) to determine or assist with the correspondence step of S5 (see also steps S5 and S5b in FIG. 10); and (iii) using a guidance device, such as the guidance device 105, to verify and/or assist with needle placement when performing ablation for the patient (see step S6 in FIG. 10). In one or more embodiments of the present disclosure, at least one embodiment of a method for performing ablation planning or ablation performance is to use such calibration device(s) and/or locator device(s) to increase or maximize the success of the ablation procedure depending on one or more variables, such as, but not limited to, needs of the patient, characteristics of the lesion/tumor, if movement of the patient is needed during the procedure, etc. In one or more embodiments of the present disclosure, such calibration device(s) and/or locator device(s) assist a clinician in finding a medial axis or center line of the target biological object, such as a lesion or tumor.

In one or more embodiments, workflow for a particular procedure, such as guidance planning and/or performance and/or ablation planning and/or ablation performance, may be combined with segmentation, registration and differential image view steps to provide better differential images (such as, but not limited to, segmentation, registration and differential image steps disclosed in PCT/US2018/020752, which is incorporated by reference herein in its entirety) and the manipulation of registration result(s) as discussed herein, which avoid the generation of misleading artifacts in images and/or avoid other issues with procedure-related problems. Differential images are a quick way to give clinicians feedback of needle guidance and/or ablation results. While thermal maps may be used in one or more embodiments, such thermal maps may be affected by environmental changes, such as blood flow, and measurements may not be easily localized depending on the circumstances. Various types of ablation may be used in one or more embodiments (e.g., cryoablation, microwave ablation, laser ablation, etc.). While cryoablation may be used, iceballs may form, and are very visible under MRI. Ultrasound may be used in one or more of the methods discussed herein for navigation, and some indication of an ablation result may be obtained from the same tool. However, ultrasound images may be noisy and may be hard to quantitatively measure. Regardless of which detection or monitoring tool/technique is employed, the integration of the workflow with segmentation, registration and differential image view steps reduces and/or avoids such issues to provide a useful differential image or images for clinicians to use in one or more procedures (e.g., ablation, radiotherapy, etc.).

For medical procedures, such as ablation, one probe ablation or multi-probe ablation may be performed. For multi-probe ablation, serial or parallel multi-probe ablation may be performed. In serial ablation, ablation is done in sequence of one probe being inserted, ablated, confirmed, then another probe being inserted, ablated, confirmed, and repeating such steps if more probes are needed. In parallel ablation, all probes are inserted before ablation starts. Clinicians may decide which ablation approach is chosen. No matter which approach is chosen, a confirmation stage is needed after the ablation is done. Based on information from each confirmation, a clinician may determine whether additional ablation is needed, and, if so, where to plan for the next probe to be used. Confirmation also provides clinicians with an indication as to whether the margin is reached or overreached to evaluate the results of the ablation procedure.

To aid clinicians in performing confirmation steps, one or more embodiments of the present disclosure may include confirmation with margin view so that confirmation or any other determination process requiring clear image feedback may be performed more effectively (such as, but not limited to, confirmation steps disclosed in PCT/US2018/020752, which is incorporated by reference herein in its entirety). While quantitative measure of coverage is useful, a visual quick assessment is also very useful in one or more applications. The margin view gives a better view than the common overlay of before and after ablation images to more easily and effectively determine the success of the ablation process. In one or more embodiments, the target(s), such as lesion(s) or tumor(s) may be segmented before and after ablation occurs, and differentiation between the two sets of segmented target images may be determined. Thereafter, the differential may be overlaid on the after-ablation images to evaluate the ablation process. Additionally or alternatively, one or more method(s) of the present disclosure may further include performing ablation planning and/or performance with the guidance device 105 as shown in FIG. 7 and in FIGS. 9-10. One or more embodiments of methods for evaluating or determining a margin view may include, but are not limited to, one or more of the following: (i) loading images (e.g., from a scanner, a PACS or other scanning device/system, or using a fresh or newly scanned image) (see step S1 in FIGS. 9-10); (ii) visualizing images (e.g., such as by showing multiple panes (views) (e.g., each view may represent a different aspect of the image); as described above for step S2 in FIGS. 9-10; (e.g., in medical image software, such as, for example, the application shown in PCT/US2018/020752, which is incorporated by reference herein in its entirety); as otherwise described herein; etc.) (see step S2 in FIGS. 9-10); (iii) performing device registration (also referred to herein as device calibration) to make a correct correspondence or alignment between an image and real world dimensions for a patient (see e.g., steps S5 and/or S5b of FIG. 9 and/or FIG. to which may be incorporated into or used as a configuration or registration step; see also, device registration as discussed in PCT/US2018/020752, which is incorporated by reference herein in its entirety; see also, aforementioned registration result visualization and manipulation steps (such as, but not limited to, the steps shown in FIG. 3); (iv) identify a target or target(s), such as a zone or biological object (see step S3 of FIGS. 9-10); (v) segmenting the identified targets (at one reference point in the planning or procedure (e.g., before moving a needle, before performing ablation, before performing the next iterative or incremental planning step (either during the procedure or in simulation or planning), before moving a patient, etc.)—also referred to herein as "targets (1)", i.e., the targets identified at stage (1)); (vi) performing an incremental planning or performance step (e.g., move a needle, insert a new probe or needle, perform ablation, perform the next planning step, moving a patient, etc.); (vii) re-scanning the targets or obtaining newly scanned images of the targets after performing the incremental planning or performance step; (viii) visualizing images (e.g., such as by showing multiple panes (views) (e.g., each view may represent a different aspect of the image); as described above for step S2 in FIGS. 9-10; as otherwise described herein; etc.)); (ix) identifying a target or target(s), such as a zone or biological object (which may be the same or similar to step S3 of FIGS. 9-10 such that the above details regarding same are not repeated herein); (x) segmenting the re-scanned targets (at a second reference point in the planning or procedure (e.g., after moving a needle, after moving or adding a probe, after performing ablation, after performing the next iterative or incremental planning step (either during the procedure or in simulation or planning), etc.)—also referred to herein as "targets (2)", i.e., the targets as re-scanned at stage (2) after stage (1)); (xi) performing image registration (e.g., before conducting differentiation of current images and previous images); (xii) performing differentiation of current images (e.g., images of stage (2)) and previous images (e.g., images of stage (1)) to enhance the view of the effect of the procedure (e.g., ablation (especially when using microwave or radiofrequency (RF) ablation (in one or more embodiments, differentiation subtraction may not be needed for cryoablation)), radiotherapy, etc.); and (xiii) overlaying the differential on the current images (e.g., images of stage (2)). Image segmentation and registration may be performed using any method known to those skilled in the art, such as a clinician, and may be performed using the aforementioned registration result(s) visualization and manipulation steps.

The image differentiation may be used to enhance the visualization of a needle (or other medical device) guidance result and/or an ablation result, monitor probe progression during insertion, or to track any other incremental step in a procedure (e.g., ablation, radiotherapy, etc.). By way of example, a concept of such an enhancement after performing ablation is shown in PCT/US2018/020752, which is incorporated by reference herein in its entirety. The target or target zone of a biological object (such as a lesion or tumor) is surrounded by an ablation zone or ablated zone (once ablation is performed). As such, in one or more embodiments, such as when performing differentiation and overlaying the differential on the current image(s) of stage (2) or final images, a margin map is formed. The margin map may be used by a clinician to determine whether or not to edit a procedure plan and/or to evaluate whether the plan or procedure is optimal (e.g., the best option available) or has been successful (and to gauge how successful). This improved ability to measure success is good for feedback (such as for the clinician, patient, hospital, other clinicians consulting such results, etc.), and provides an outcome oriented application in one or more embodiments of the present disclosure. For example, the percent of the margin (and/or other metrics of the margin) may be used to indicate how well the procedure went. A minimum or a maximum of the margin view or map may be set or predetermined by a clinician. The treatment or target zone may be displayed, overlaid on the target zone or target object (segmented), e.g., a tumor or lesion.

Additionally or alternatively, clinicians may perform simulations with one or more embodiments of the planning methods/software of the present disclosure to create an optical plan, to accommodate one or more variables (e.g., patient movement during the procedure, tissue deformations, etc.), and to evaluate the potential outcome. By way of at least one example, a simulation of a target zone (e.g., in an example where the medical procedure is ablation, the simulation may be an ice ball for cryoablation, a balloon for microwave ablation, etc.) may be conducted. By way of another example, a simulation may be performed to mimic tissue deformation. For example, if clinicians segmented an organ or tumor (suppose an oval shape for purposes of the example simulation), the medial axis algorithm may take the segmented object as input and generate a medial axis output (typically it is a curve), which may be overlaid on the segmented object. By dragging and manipulating the medial axis curve, the curve may change its shape and location in space. Due to the fact that a volume may be reconstructed from a medial axis curve, the deformation may be simulated or obtained by dragging and manipulating the medial axis.

One or more embodiments of the guidance planning and performance and/or visualization and manipulation of registration result(s) apparatuses and systems, and methods and storage mediums of the present disclosure may operate to reduce the number of iterations for the determination of the insertion point(s) and trajectory of the needle(s) and/or probe(s) after being inserted into the entry point(s), especially due to the improved and efficient registration method (s) discussed herein. This is beneficial for reducing exposure to radiation when dealing with CT scans and reduces the total time of scanning when dealing with any type of scan, including, but not limited to, CT, MRI or otherwise. In one or more embodiments, registration with fiducial markers (such as a sticker grid as aforementioned, the fiducial markers 209, any or all of fiducials F-1 through F-8, etc.) may be used on the patient at or near an insertion point before conducting a CT/MRI scan. This registration step helps to accurately correlate physical dimensions to what to see in the scanned images.

After a target zone is identified, clinicians may pick up a point or a few points within the target zone as target point(s). From there on, in the case of ablation, an ablation zone (for example iceball) may be defined on or around the target zone (e.g., in the case of the iceball example, the ball may be centered on the ablation zone). In other medical procedures, a guidance zone for one or more needles may be more generally defined on or around the target zone.

While clinicians may pick target points by trial and error, such trial and error leads to inefficiencies, such as, but not limited to, longer procedure time, more invasive and repeated steps (e.g., needle or probe insertion/movement), lack of accuracy, etc.

Figure 11:
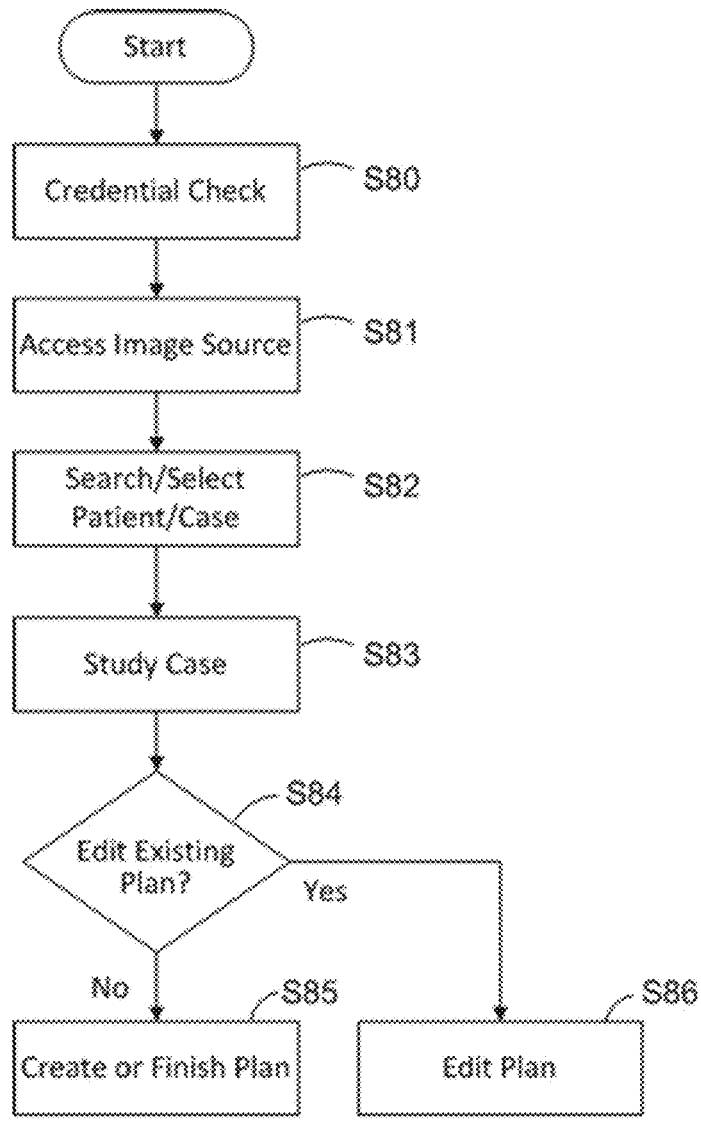
FIG. 11 is a flow chart showing at least another embodiment of a method for performing a medical procedure (e.g., ablation and/or needle guidance planning and/or performance) using a security or credential check in accordance with one or more aspects of the present disclosure.

Additionally, in one or more embodiments, a security check may be included to perform the check in the surgical room prior to the needle guidance planning and/or procedure to ensure maximal security and safety. To make the security check convenient for clinicians (who have scrubbed in and are wearing gloves at that point and may not be able to use their hands for performing the security check), iris and/or face recognition may be incorporated. Such iris and/or face recognition based approaches may be preferred to control access to patient data (CT scan for example) and communication with peers. While other forms of security control may be used, forms, such as, but not limited to, typing a password, finger print scan, or other forms that require the use of a clinician's hand(s), may not be preferred because a clinician's hands may be sterilized. Once logged in, clinicians may be able to access patient data and communication with peers. FIG. 11 depicts where this checking step may be employed for access image data to create or edit a plan for any medical procedure, such as ablation, cryotherapy, biopsy, etc. For example, prior to any method disclosed herein for performing needle guidance planning and/or performance or ablation planning and/or performance, the credential check (step S80 of FIG. 11) may be performed to make sure that the clinician is permitted to access patient data and communication with other clinicians. Once the clinician passes the credential check (S80), then the clinician has access to the image source (see step S81 of FIG. 11), and may search or select a patient or case file (see step S82 of FIG. 11). Once the patient or case file is retrieved in step S82, the clinician may study the case (see step S83 of FIG. 11), and may determine whether edit(s) to an existing procedure plan (e.g., an ablation plan, a radiotherapy plan, a biopsy plan, needle guidance plan, etc.) are required or not (see step S84 in FIG. 11). If "No" edits to an existing plan are needed (e.g., a plan is finished, a plan does not exist, etc.), the clinician may create or finish a plan for the procedure (see step S85 of FIG. 11). If "Yes" and edits to an existing plan are needed, the clinician may edit the previously created plan (see step S86 of FIG. 11). These steps may be used in addition to any of the aforementioned methods for performing guidance planning and/or performance, for ablation planning and/or ablation performance, for radiotherapy planning and/or performance, for guiding multiple needles or multiple ablation probes, for visualizing and manipulating registration result(s), or other procedural methods as may be useful.

Figure 12:
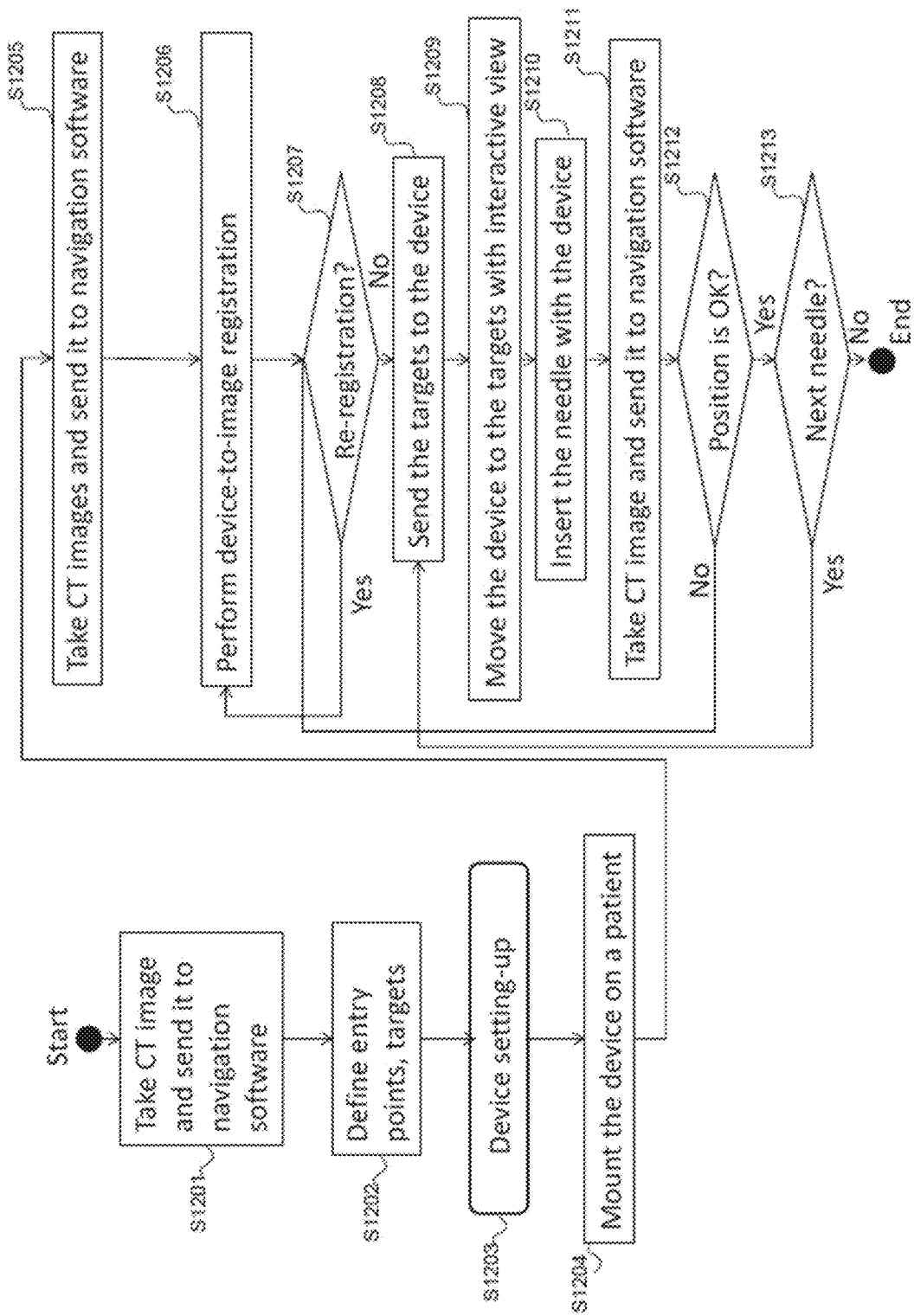
FIG. 12 is a flow chart illustrating a process for guidance of a needle using a medical guidance device and/or system in accordance with one or more aspects of the present disclosure.

FIG. 12 is a flowchart illustrating a process for guidance of a needle or needles using the medical guidance device 105. In step S1201, an operator takes medical images using the medical imaging device 5. The medical imaging device 5 is a CT scanner in this particular embodiment, and sends the CT images to the first processor 1201 of the computer 2 as aforementioned.

At step S1202, with the CT images, the operator defines targets for percutaneous intervention with a needle-like medical tool and the skin entry point. At the same time, by connecting the target to the skin entry point, the operator can determine the plane for the trajectory of insertion of the needle-like medical tool using at least the first processor 1201 (and any images and/or software displayed on the aforementioned display 1209 of the computer 2). Also, in this step, the operator marks the skin entry point on the patient using, for example, grid visible markers on the patient as aforementioned.

In step S1203, the operator sets up the system 10, including the device 105, to calibrate the system to and/or one or more components thereof, and sets a proper initial state of the medical guidance device 105. Additionally, the first processor 1201 may set up, synchronize and/or otherwise figure out the orientation, for example, between the encoder sensor 203 and the encoder scale 204.

After the setting up the device 105, in Step S1204, the operator mounts the medical guidance device 105 onto the patient aligning a predetermined portion (e.g., a center) of the device 105 to the skin entry point. When an adhesive marker is being utilized, the operator may align a center marker to the skin entry point and then adhere the medical guidance device 105 in place via an adhesive. In one or more embodiments, the user then may remove a peel-away portion of the adhesive marker to expose the patient's skin.

In Step S1205, after the device mounting, the user takes images (e.g., CT images) including the medical guidance device 105 and sends the CT images to the first processor 1201 (and related navigation or guidance software for processing the data as needed). Using the CT images with the medical guidance apparatus 105 showing, in Step S1206, the user conducts device-to-image registration. In this step, the first processor 1201 (e.g., using guidance or navigation software) recognizes the position and orientation of the medical guidance device 105 on the patient in the CT images, i.e., in the coordinate of the CT image, by using fiducial markers (e.g., the fiducial markers 209, any or all of fiducials F-1 through F-8, etc.) or fiducial markers located on the corners of the fixed portion 205. This fiducial marker detection may be manually performed by user instruction with a user interface or, may be fully automated by using a computer algorithm via the first processor 1201 and/or the second processor 1201', such as, but not limited to, the aforementioned registration visualization and manipulation of registration result(s) algorithm (see e.g., FIG. 3). The detected fiducial markers are compared with the designed geometrical configuration of the fiducial markers in the medical guidance device 105, then the first processor 1201 and/or the second processor 1201' (e.g., using guidance or navigation software) may recognize the position and the orientation of the medical guidance device 105 in CT images. The navigation software may also reflect the plan of the trajectory with two device parameters, which are angular position of the moveable portion 206 and insertion angle on the guide of the arc member 207 and/or the arc member 207 at this step.

In step S1207, the user may be asked whether the device-to-image registration is appropriate or not by the first processor 1201 and/or the second processor 1201' (e.g., via the navigation software displayed on the display 1209). This step may correspond to or include aforementioned steps S109 through S112. If not ("No" in Step S1207 or "NO" in step S109), the operator may conduct Step S1206, and/or aforementioned steps S110 through S104-S108, to perform the device-to-image registration again.

If the device-to-image registration is appropriate ("Yes" in Step S1207 or "YES" in Sill), flow proceeds to Step S1208 or step S112 where the user may send the target device parameters to the first processor 1201 and/or the second processor 1201' (e.g., by registering the device space to image space). In one or more embodiments, device space (or device coordinate space) may be a coordinate space that a virtual model (e.g., a CAD model) is in when it is loaded into needle guiding software and/or when it is processed by one or more processors discussed herein (e.g., including, but not limited to, the first processor 1201, the second processor 1201', etc.) In one or more embodiments, image space may be the coordinate space that the image(s) are acquired in which may be different than the virtual model (e.g., the CAD model) coordinate space. For example, when device space is different from image space, one of the goals of registration may be to detecting fiducial points in image space and using those fiducial points to rotate and translate the virtual model (e.g., the CAD model) to match the image space.

Afterwards in Step S1209, the operator may manually rotate the arc member 207 via the moveable portion 206 of the device 105 while the first processor 1201 and/or the second processor 1201' (e.g., using guidance or navigation software) interactively updates the cross-sectional image on the guide surface by using the real-time angular position of the movable portion 206. Also, the first processor 1201 and/or the second processor 1201' may compare the real-time angular position of the moveable portion 206 with the target angular position. Once the moveable portion 206 reaches the target angular position, the first processor 1201 and/or the second processor 1201' indicates the end of targeting of the moveable portion 206 of the device 105. Then, the first processor 1201 and/or the second processor 1201' (e.g., via guidance or navigation software displayed on the display 1209) informs the user of the end of targeting or guidance.

Upon establishing the target angular position of the moveable portion 206 of the device 105, in Step S1210, the user picks the specific angular reference mark (or other indicator mark being used in any particular embodiment) indicated by the target insertion angle on the arc 207 of the device 105 and with the specific angular reference mark (or other indicator), the user inserts the needle-like medical tool from the skin entry point to the target. In the case of the medical guidance apparatus device 105 (see various embodiment examples in FIGS. 1-2B and 4-8), the operator may slide the needle-like medical tool along the guide surface of the arc 207 (see FIGS. 1-2B) until reaching the appropriate reference mark (or other used marker). In doing so the user may apply force. However, due to the structural advantages discussed above provided by the closed/monolithic structure of the guide and/or of the movable portion 206 of the device 105, the arc portion 207 is able to fully support the force without deflection or bending. Variations may be made to the device 105 in accordance with one or more features of the present disclosure. For example, other types of guidance devices 105 may be used, such as those discussed in U.S. Provisional Patent Application No. 62/764,849, filed on Aug. 15, 2018, the entirety of which is incorporated by reference herein, and/or as discussed in U.S. Provisional Patent Application No. 62/875,243, as discussed in U.S. Provisional Patent App. No. 62/764,820, and/or as discussed in U.S. patent application Ser. No. 16/539,769, the applications of which are incorporated by reference herein in their entireties.

In Step 1211, after the first attempt of the insertion, the user takes CT images of the inserted needle-like medical tool, the medical guidance device 105, and the CT images and sends them to the first processor 1201 and/or the second processor 1201' (and any guidance or navigation software being used). With the CT images of the inserted needle-like medical tool, the user evaluates the position of the inserted needle-like medical tool.

In step S1212, the position of the inserted needle-like medical tool is checked and if the user thinks the position is suboptimal ("No" in Step S1212), flow proceeds back to Step S1208 where the user can update the trajectory to improve the position of the needle-like medical tool with the first processor 1201 and/or the second processor 1201' (e.g., by using guidance or navigation software such as discussed in U.S. Provisional Patent Application No. 62/764,849, as discussed in U.S. Provisional Patent Application No. 62/875,243, as discussed in U.S. Provisional Patent App. No. 62/764,820, and/or as discussed in U.S. patent application Ser. No. 16/539,769, the applications of which are incorporated by reference herein in their entireties). At the same time, with the latest CT image, the user finds the dislocation of the target, skin entry point and the medical guidance device 105 and updates the registered position and orientation of the medical guidance device 105. Thus, the user can conduct the device-to-image registration with the latest CT images. By updating the device-to-image registration in this way and/or using the aforementioned method steps (see e.g., FIG. 3 and related discussions), the user can reduce discrepancy of the actual geometrical relationship between the medical guidance device 105 and the target. Specifically, since the medical guidance device 105 is mounted on the patient and can move with the patient body together, the update of the device-to-image registration can effectively compensate rigid dislocation of the patient from the older CT images.

With updated plane of the trajectory and the device-to-image registration, the user can perform another attempt of the insertion with the same steps as in the first attempt.

In step S1212, if the position of the inserted needle-like medical tool is checked and the user is satisfied with the results ("Yes" in Step S1212), flow continues to Step S1213. In Step S1213, a determination is made as to whether insertion of another needle-like medical tool is needed. If insertion of another needle-like medical tool is needed ("Yes" in Step S1213) flow returns back to Step S1205. If insertion of another needle-like medical tool is not needed ("No" in Step S1213) flow is complete. When inserting another needle-like medical tool, the user may decouple the guide or the movable portion 206 from the fixed portion 205 as necessary without needing to unmount the fixed portion 205 of the aforementioned embodiment examples of the device 105. In the case of inserting another needle-like medical tool in another guide, preferably the user may remove the previous needle-like medical tool from the instrument holder 70.

Once all of the needle-like medical tools have been inserted, the operator may decouple the guide or the arc 207 from the moveable portion 206. Once the guide or the arc 207 has been decoupled and can be freely lifted away, the operator may orient the guide such that each of the needle-like medical tools passes through the gap or opening of the guidance device 105. Thus, the guide may be completely removable from the procedure site, even when the needle-like medical tool is tethered, such as for percutaneous ablation probes. Similarly, one or more portions of the other embodiments of the device 105 may be removed as needed (e.g., the movable portion 206) as aforementioned.

In at least one embodiment, the computer 2, 2' operates to control the medical procedure (e.g., needle guidance, ablation, biopsy, etc.) planning and/or performance, probe or needle guidance planning and/or performance, and/or visualization and manipulation of registration result(s) device(s), system(s) and/or storage medium(s), and may display the scanned image(s) and the procedure plan (e.g., on a monitor or screen such as a display, screen or monitor 1209 as shown in the computer 2 of FIG. 7, in the computer 2 of FIG. 13 and/or the computer 2' of FIG. 14 as further discussed below). The console or processor 2, 2' (or the first processor 1201 of the console or computer 2, 2') or the second processor 1201' of the device 105 may be used to control any portions of the system 10 of FIG. 7, for example, including, but not limited to, the medical device 1, the guidance device 105, the PACS system 4, the image scanner and console 5 (e.g., CT scanner), etc. The processor 1201 of the console 2, 2' and/or the second processor 1201' of the device 105 may be used to perform any of the aforementioned method(s) or algorithm(s), and may use one or more feature(s) of such method(s) or algorithm(s) in any combination desired by a clinician for a predetermined procedure (e.g., medical procedure (e.g., ablation, biopsy, etc.) planning and/or performance; needle or probe guidance; a combination thereof; etc.). For example, the CPU 1201 of the processor 2, 2' may load images (e.g., from a scanner or PACS 4) in step S1 of FIGS. 9-10, and may display such images to allow the clinician to visualize the images (e.g., in step S2 of FIGS. 9-10). The computer, such as the console or computer 2, 2', may receive data from a device (e.g., such as the guidance device 105, an image scanner 5, a PACS 4, etc.) or a system via a network interface (see e.g., communication interface 1205 and network 1206 as shown in FIG. 13 or Network I/F 1212 as shown in FIG. 14), or the computer, such as the console or computer 2, 2', may obtain a set of imaging conditions using the operation input from the mouse or keyboard (see e.g., the keyboard 1210 as shown in FIG. 13 or the mouse 1211 and/or keyboard 1210 as shown in FIG. 14).

Unless otherwise discussed herein, like numerals indicate like elements. For example, while variations or differences exist between the methods, devices, systems or storage mediums, such as, but not limited to, the system to, the communication devices and methods shown in FIGS. 7-14, etc., one or more features thereof may be the same or similar to each other, such as, but not limited to, the use of one or more component(s) thereof (e.g., the console 2, the console 2', the medical device 1, the guidance device 105, the PACS 4, the CT scanner 5, any or all of the components of FIGS. 1-2B, FIGS. 4-8, FIGS. 13-14, etc.). Those skilled in the art will appreciate that the method steps disclosed herein may operate in the same or similar fashion to those like-numbered elements of one or more other methods or algorithms as discussed herein. Those skilled in the art will appreciate that alternative embodiments of the system to, may be used while having other variations as discussed herein for performing one or more methods discussed herein. Likewise, while the console or computer 2 may be used in one or more systems or with one or more methods disclosed herein, one or more other consoles or computers, such as the console or computer 2', may be used additionally or alternatively.

There are many ways to plan for and perform a medical procedure (e.g., needle guidance, ablation, biopsy, visualization and manipulation of registration result(s), etc.) or any other measurement or determination discussed herein, digital as well as analog. In at least one embodiment, a computer, such as the console or computer 2, 2', may be dedicated to control and monitor the devices, systems, methods and/or storage mediums described herein.

The electric signals used for imaging may be sent to one or more processors, such as, but not limited to, a computer or processor 2 (see e.g., FIGS. 7 and 13), the first and second processors 1201, 1201' (see e.g., FIG. 8), a computer 2' (see e.g., FIG. 14), etc. as discussed further below, via cable(s) or wire(s), such as, but not limited to, the cable(s) or wire(s) 113 (see FIG. 13). Additionally or alternatively, the electric signals, as aforementioned, may be processed in one or more embodiments as discussed above by any other computer or processor or components thereof. The computer or processor 2 as shown in FIGS. 7 and 13 may be used instead of any other computer or processor discussed herein (e.g., computer or processors 1201, 1201', 2', etc.), and/or the computer or processor 2, 2' may be used instead of any other computer or processor discussed herein (e.g., computer or processor 1201, 1201', etc.). In other words, the computers or processors discussed herein are interchangeable, and may operate to perform any of the multiple imaging modalities feature(s) and method(s) discussed herein, including using, controlling, and changing a GUI or multiple GUI's.

Various components of a computer system 2 (see e.g., the console or computer 2 as shown in FIG. 7) are provided in FIG. 13. A computer system 2 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 7). In addition, the computer system 2 may comprise one or more of the aforementioned components. For example, a computer system 2 may include a CPU 1201, a RAM 1203, an input/output (I/O) interface (such as the communication interface 1205) and a bus (which may include one or more lines 1213 as a communication system between components of the computer system 2; in one or more embodiments, the computer system 2 and at least the CPU 1201 thereof may communicate with the one or more aforementioned components of an ablation performance and/or planning and/or needle or probe guidance device or system, such as, but not limited to, the system to discussed herein above, via one or more lines 1213 or wirelessly through a first wireless circuit 1205, 1212 and a second wireless circuit 1205, 1212, and/or through communication or network interfaces that include wired and wireless structural attributes and features), and one or more other computer systems 2 may include one or more combinations of the other aforementioned components. The CPU 1201, 1201' is configured to read and perform computer-executable instructions stored in a storage medium. The computer-executable instructions may include those for the performance of the methods and/or calculations described herein.

The system to may include one or more additional processors in addition to CPU 1201, and such processors, including the CPU 1201, may be used for performing ablation planning and/or performance and/or multiple needle or multiple ablation probe guidance. The system to may further include one or more processors connected via a network connection (e.g., via network 1206). The CPU 1201 and any additional processor being used by the system 2 or the system to may be located in the same telecom network or in different telecom networks (e.g., performing needle guidance, medical procedure (e.g., ablation, biopsy, etc.) planning and/or performance technique(s) may be controlled remotely or wirelessly).

The I/O or communication interface 1205 provides communication interfaces to input and output devices, which may include the medical device 1, the guidance device 105, the PACS 4, the CT scanner 5, a microphone, a communication cable and a network (either wired or wireless), a keyboard 1210, a mouse (see e.g., the mouse 1211 as shown in FIG. 14), a touch screen or screen 1209, a light pen and so on. The Monitor interface or screen 1209 provides communication interfaces thereto.

Any methods and/or data of the present disclosure, such as the methods for performing ablation planning and/or performance, radiotherapy, guidance of needle(s) and/or probe(s), visualization and manipulation of registration result(s) or otherwise as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 14), SRAM, etc.), an optional combination thereof, a server/database, etc. may be used to cause a processor, such as, the processor or CPU 1201 of the aforementioned computer system 2 and/or the system to, the second processor 1201' of the device 105, etc., to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 2, the processor 1201' of the device 105, etc., as described above may be achieved utilizing suitable hardware, such as that illustrated in the figures. Functionality of one or more aspects of the present disclosure may be achieved utilizing suitable hardware, such as that illustrated in FIGS. 1-2B, 4-8, FIG. 13 and/or FIG. 14. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201, 1201' (as shown in FIGS. 8, 13 and/or 14) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 2' is shown in FIG. 14. The computer 2' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 2' includes a display 1209. The computer 2' may connect with the medical device 1, the guidance device 105, the PACS 4, the CT scanner 5, communication devices (e.g., to discuss the procedure with peers, clinicians, etc.) via the operation interface 1214 or the network interface 1212 (e.g., via wired or wireless connection). The operation interface 1214 is connected with an operation unit such as a mouse device 1211, a keyboard 1210 or a touch panel device. The computer 2' may include two or more of each component.

In at least one embodiment, at least one computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 2, 2', communicates with one or more other system components (e.g., the medical device 1, the guidance device 105, the PACS 4, the CT scanner 5 or other type of scanner, of system to or other device or system being used for medical procedure (e.g., needle guidance, ablation, biopsy, visualization and manipulation of registration result(s), etc.) planning and/or performance) to perform imaging, planning and/or performance.

The monitor or display 1209 displays the plan and performance and/or guidance steps (e.g., in real time), and may display other information about the imaging condition or about an object to be imaged and operated on during the procedure. The monitor 1209 also provides a graphical user interface for a user to operate an ablation planning and/or performance and/or needle guidance or ablation (or other medical procedure) probe guidance device or system (e.g., the system to). An operation signal is input from the operation unit (e.g., such as, but not limited to, a mouse device 1211, a keyboard 1210, a touch panel device, etc.) into the operation interface 1214 in the computer 2', and corresponding to the operation signal the computer 2' instructs the system (e.g., the system to) to set or change the imaging, planning and/or performance condition(s), and to start or end any portion of any of the method(s) discussed herein.

The present disclosure and/or one or more components of devices, systems and storage mediums, and/or methods, thereof also may be used in conjunction with any suitable optical assembly including, but not limited to, ablation technology, such as in U.S. Pat. No. 9,867,673; U.S. patent application Ser. Nos. 16/027,093, 15/836,141, and 15/727,978; U.S. Provisional Patent Application No. 62/764,849, filed on Aug. 15, 2018; U.S. Provisional Patent App. No. 62/764,820, filed Aug. 15, 2018; U.S. Provisional Patent App. No. 62/875,243, filed Jul. 17, 2019; U.S. patent application Ser. No. 16/539,769, filed Aug. 13, 2019; U.S. Pat. Pub. No. 2019/0105109, published on Apr. 11, 2019; U.S. Pat. Pub. No. 2019/0008591, published on Jan. 10, 2019; U.S. Pat. Pub. No. 2018/0098819, published on Apr. 12, 2018; App. No. PCT/US2018/020752; and App. No. PCT/US15/40336, each of which patent(s), patent publication(s) and application(s) are incorporated by reference herein in their entireties.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

What is claimed is:

1. A medical guidance device comprising:
a first portion including a portion defining an opening, the first portion including one or more fiducial markers that operate to be used to align, and confirm alignment of, the first portion on a patient via visualization and manipulation of one or more registration results of the medical guidance device;
a second movable portion that is rotatably mateable with the first portion; and
one or more processors that operate to:
acquire and/or load one or more images;
perform a device-to-image registration to detect locations of the one or more fiducial markers on a detected fiducial plane of the one or more images and to obtain the one or more registration results of the medical guidance device;
match the detected fiducial locations of the one or more fiducial markers to a template and calculate a first registration error for the one or more fiducial markers relative to the template;
reconstruct the detected fiducial plane through a multi-planar reconstruction;
reconstruct one or more oblique slices relative to the detected fiducial plane through each detected fiducial location and overlay the detected fiducial locations on the one or more reconstructed oblique slices;
calculate a second registration error between the locations of the one or more fiducial markers on the one or more images and the detected fiducial locations on the one or more reconstructed oblique slices and determine whether the second registration error is equal to or above a threshold; and
in the event that the second registration error is below the threshold, then add, delete, and/or move the detected fiducial locations in the one or more reconstructed oblique slices; or
in the event that the second registration error is equal to or above the threshold, then register a device space to an image space.

2. The medical guidance device of claim 1, wherein:
(i) the one or more fiducial markers operate to align, and confirm alignment of, the first portion on the patient in a targeted orientation or in a predetermined location, or over a surgical site, via the device-to-image registration of the medical guidance device; and
(ii) the second movable portion includes:
a frame defining an opening that operates to overlay the opening of the first portion when the first portion and the second movable portion are mated with each other;
an arc member attached to the frame; and
a holder slidably attached to the arc member,
wherein the holder operates to hold one or more medical tools to be guided by the medical guidance device.

3. The medical guidance device of claim 2, wherein the medical guidance device operates to be or is adapted to be placed or secured onto the patient in the targeted orientation or in the predetermined location, or over the surgical site, and wherein the one or more medical instruments or tools operate to be inserted through an insertion point of a surface in a case where the second registration error is equal to or above the threshold.

4. The medical guidance device of claim 2, wherein one or more of the following:
the arc member includes a guidance surface having one or more reference marks or a reference scale that operates to aid in the guidance of the one or more medical tools;
the holder comprises one or more grooves for accepting the one or more medical tools therein; and
the holder comprises a plurality of grooves where each groove of the plurality of grooves operates to hold a different medical tool therein.

5. The medical guidance device of claim 1, wherein one or more of the following:
the first portion operates to be fixed to the patient in a targeted orientation or in a predetermined location, or over a surgical site, for performing a medical procedure with one or more medical tools;
the one or more fiducial markers operate to orient and position the first portion and/or the medical guidance device on the patient; and
the one or more fiducial markers are used to determine whether the one or more registration results indicate that the medical guidance device is positioned in a targeted orientation or in a predetermined location, or over a surgical site, on the patient or not.

6. The medical guidance device of claim 1, wherein one or more of the following:
the template is a virtual computer-aided drawing or design (CAD) model of the medical guidance device with known fiducial locations of the one or more fiducial markers; and
the first registration error is calculated as the mean square distance of points between the detected fiducial markers or locations of the one or more fiducial markers in the one or more images or in the one or more reconstructed oblique slices and the template matched fiducial locations of the one or more fiducial markers.

7. The medical guidance device of claim 1, wherein one or more of the following:
the detected fiducial plane is reconstructed such that all of the one or more fiducial makers are shown in a single two-dimensional (2D) image;
the one or more reconstructed oblique slices are configured to provide a third (3D) dimension of or to the detected fiducial locations;
a representation of virtual device model mounted fiducials or fiducial marker(s) matched to the registration-detected fiducial locations is overlaid on one or more of the one or more reconstructed oblique slices; and
slice intersections of the virtual model mounted fiducials or fiducial marker(s) are an outline of a solid model of each fiducial marker on the one or more reconstructed oblique slices.

8. The medical guidance device of claim 1, wherein the detected fiducial locations are indicated by an overlaid dot or indicator on one or more of the one or more reconstructed oblique slices and/or the reconstructed fiducial plane.

9. The medical guidance device of claim 1, wherein the calculated first registration error and visual representation of registration through one or more reconstructed oblique slices provide visualization of the one or more registration results.

10. The medical guidance device of claim 1, wherein one or more of the following:
the template is a virtual model, or a virtual computer-aided drawing or design (CAD) model, of the medical guidance device with known fiducial locations;
in a case where there are mismatches beyond a predetermined error, threshold between the detected locations of the one or more fiducial markers and the matched template, where the matched template is a virtual model, made visually apparent by the one or more reconstructed oblique slices, then it is determined that the second registration error is below the threshold, and the one or more processors perform the adding, deleting, and/or moving of the detected fiducial locations in the one or more reconstructed oblique slices and recalculate matching between the template and the detected fiducial locations; and
the one or more processors are configured to reconstruct the detected fiducial plane, overlay the detected fiducial locations on the one or more reconstructed oblique slices, overlay a representation of virtual device model mounted fiducials or fiducial marker(s) matched to the registration-detected fiducial locations on one or more of the one or more reconstructed oblique slices, re-draw virtual model fiducial slice intersections, and repeat the reconstruction of the detected fiducial plane, the overlaying of the detected fiducial locations, the overlaying of the representation of the virtual device model, and the re-drawing until it is determined that the second registration error is within or equal to the predetermined error threshold and is equal to or above the threshold.

11. The medical guidance device of claim 1, wherein the medical guidance device operates to one or more of the following:
(i) allow a user to visualize and manipulate the one or more registration results of the medical guidance device to add, move, and/or delete any fiducial markers or locations such that one or more of the fiducial markers or locations are updated or manipulated;
(ii) in a case where there are one or more updated or manipulated fiducial markers or locations, automatically re-register the medical guidance device based on the updated or manipulated fiducial markers or locations;
(iii) allow the user to visualize, via the one or more processors and/or via a display, before or after a medical procedure or in real time during a medical procedure, one or more of the fiducial markers, analyze the detected fiducial marker locations, identify any undetected fiducial markers, and correlate with the second registration error;
(iv) automatically recalculate the template matching between fiducials or fiducial marker(s) detected in the one or more images and the template, or a virtual model, of the fiducials or fiducial marker(s), and recalculate the second registration error; and
(v) provide the user with a feedback on how the user manipulation of the detected fiducial locations affects the second registration error or the one or more registration results of the medical guidance device.

12. The medical guidance device of claim 1, wherein the one or more processors communicate, wirelessly or with a wired connection, with a first processor of a computer, the computer including the first processor and a first communication circuit;
the medical guidance device further includes a second communication circuit that allows the one or more processors of the medical guidance device to communicate with the first processor of the computer via the first communication circuit; and
the first processor of the computer operates to perform one or more of the operations of the one or more processors of the medical guidance device.

13. A method for guiding and controlling one or more medical instruments or tools of a medical guidance device and/or visualizing and manipulating one or more registration results of the medical guidance device, the medical guidance device comprising a first portion including a portion defining an opening, the first portion including one or more fiducial markers that operate to be used to align, and confirm alignment of, the first portion on a patient via visualization and manipulation of one or more registration results of the medical guidance device, a second movable portion that is rotatably mateable with the first portion and that is positioned to a predetermined position relative to the first portion, where the one or more medical instruments or tools are positioned to or disposed at a predetermined position upon the second movable portion, and one or more processors, the method comprising:
performing, via the one or more processors, a device-to-image, registration to detect locations of the one or more fiducial markers on a detected fiducial plane of one or more images and to obtain the one or more registration results of the medical guidance device;

matching, via the one or more processors, the detected fiducial locations of the one or more fiducial markers to a template and calculating a first registration error for the one or more fiducial markers relative to the template;

reconstructing, via the one or more processors, the detected fiducial plane through a multi-planar reconstruction;

reconstructing, via the one or more processors, one or more oblique slices relative to the detected fiducial plane through each detected fiducial location and overlaying the detected fiducial locations on the one or more reconstructed oblique slices;

calculating, via the one or more processors, a second registration error between the locations of the one or more fiducial markers on the one or more images and the detected fiducial locations on the one or more reconstructed oblique slices and determining whether the second registration error is equal to or above a threshold; and guiding and controlling the one or more medical instruments or tools and/or visualizing and manipulating the one or more registration results of the medical guidance device based on the second registration error.

14. The method of claim 13, wherein:
(i) the one or more fiducial markers operate to align, and confirm alignment of, the first portion on the patient in a targeted orientation or in a predetermined location, or over a surgical site, via the device-to-image registration of the medical guidance device; and
(ii) the second movable portion includes:
a frame defining an opening that operates to overlay the opening of the first portion when the first portion and the second movable portion are mated with each other;
an arc member attached to the frame; and
a holder slidably attached to the arc member,
wherein the holder operates to hold the one or more medical instruments or tools to be guided by the medical guidance device.

15. The method of claim 14, further comprising placing or securing the medical guidance device onto the patient in the targeted orientation or in the predetermined location, or over the surgical site,
wherein the one or more medical instruments or tools operate to be inserted through an insertion point of a surface in a case where the second registration error is equal to or above the threshold.

16. The method of claim 13, further comprising:
acquiring and/or loading, via the one or more processors, the one or more images;
in the event that the second registration error is below the threshold, then adding, deleting, and/or moving, via the one or more processors, the detected fiducial locations in the one or more reconstructed oblique slices; and
in the event that the second registration error is equal to or above the threshold, then registering, via the one or more processors, a device space to an image space.

17. The method of claim 16, wherein one or more of the following:
the template is a virtual computer-aided drawing or design (CAD) model of the medical guidance device with known fiducial locations of the one or more fiducial markers; and
the first registration error is calculated, via the one or more processors, as the mean square distance of points between the detected fiducial markers or the locations of the one or more fiducial markers in the one or more images or in the one or more reconstructed oblique slices and the template matched fiducial locations of the one or more fiducial markers.

18. The method of claim 16, wherein one or more of the following:
the detected fiducial plane is reconstructed such that all of the one or more fiducial markers are shown in a single two-dimensional (2D) image;
the one or more reconstructed oblique slices are configured to provide a third (3D) dimension of or to the detected fiducial locations;
a representation of virtual device model mounted fiducials or fiducial marker(s) matched to the registration-detected fiducial locations is overlaid on one or more of the one or more reconstructed oblique slices; and
slice intersections of the virtual model mounted fiducials or fiducial marker(s) are an outline of the solid model of each fiducial marker on the one or more reconstructed oblique slices.

19. The method of claim 16, further comprising indicating, via the one or more processors, the detected fiducial locations with or by an overlaid dot or indicator on one or more of the one or more reconstructed oblique slices and/or the reconstructed fiducial plane.

20. The method of claim 16, wherein the calculated first registration error and visual representation of registration through one or more reconstructed oblique slices provide visualization of the one or more registration results.

21. The method of claim 16, wherein the template is a virtual model, or a virtual computer-aided drawing or design (CAD) model, of the medical guidance device with known fiducial locations; and further comprising one or more of the following:
in a case where there are mismatches beyond a predetermined error, threshold between the detected locations of the one or more fiducial markers and the matched virtual model made visually apparent by the one or more manually or reconstructed oblique slices, determining, via the one or more processors, that the second registration error is below the threshold, performing the adding, deleting, and/or moving steps, via the one or more processors, and recalculating, via the one or more processors, matching between the template and the detected fiducial locations; and
via the one or more processors, reconstructing the detected fiducial plane, overlaying the detected fiducial locations on the one or more reconstructed oblique slices, overlaying a representation of virtual device model mounted fiducials or fiducial marker(s) matched to the registration-detected fiducial locations on one or more of the one or more reconstructed oblique slices, re-drawing virtual model fiducial slice intersections, and repeating the reconstruction of the detected fiducial plane, the overlaying of the detected fiducial locations, the overlaying of the representation of the virtual device model, and the re-drawing steps until it is determined that the second registration error is equal to or above the threshold.

22. The method of claim 16, further comprising one or more of the following:
(i) allowing, via the one or more processors, a user to visualize on a display and manipulate the one or more registration results of the medical guidance device by adding, moving, and/or deleting any fiducial markers or locations such that one or more of the fiducial markers or locations are updated or manipulated;

(ii) in a case where there are one or more updated or manipulated fiducial markers or locations, automatically re-registering, via the one or more processors, the medical guidance device based on the updated or manipulated fiducial markers or locations;

(iii) allowing, via the one or more processors, the user to visualize, via the one or more processors and/or via a display, before or after a medical procedure or in real time during a medical procedure, one or more of the fiducial markers, analyze the detected fiducial marker locations, identify any undetected fiducial markers, and correlate with the second registration error;

(iv) automatically recalculating, via the one or more processors, the template matching between fiducials or fiducial marker(s) detected in the one or more images and the template, or a virtual model, of the fiducials or fiducial marker(s), and recalculating the second registration error; and (v) providing, via the one or more processors, the user with a feedback on how the user manipulation of the detected fiducial locations affects the second registration error or the one or more registration results of the medical guidance device.

23. The method of claim 13, further comprising:

causing, via the one or more processors, a display to display the one or more images taken including the one or more medical instruments or tools and including the medical guidance device;

designating, via the one or more processors, at least one target position in the displayed one or more images, at which the one or more medical instruments or tools is/are to be positioned, in response to receiving a user input for selecting a position in the displayed one or more images; and guiding the one or more medical instruments or tools to or into the at least one target position.

24. A non-transitory storage medium storing at least one program to be executed by one or more processors to perform a method for visualizing and manipulating one or more registration results and/or for guiding and controlling one or more medical instruments or tools of a medical guidance device, wherein the medical guidance device comprises a first portion including a portion defining an opening, the first portion including one or more fiducial markers that operate to be used to align, and confirm alignment of, the first portion on a patient via visualization and manipulation of one or more registration results of the medical guidance device, and a second movable portion that is rotatably mateable with the first portion and that is positioned to a predetermined position relative to the first portion, where the one or more medical instruments or tools are positioned to or disposed at a predetermined position upon the second movable portion, the method comprising:

performing a device-to-image registration to detect locations of the one or more fiducial markers on a detected fiducial plane and to obtain the one or more registration results of the medical guidance device;

matching the detected fiducial locations of the one or more fiducial markers to a template and calculating a first registration error for the one or more fiducial markers relative to the template;

reconstructing the detected fiducial plane through a multi-planar reconstruction;

reconstructing one or more oblique slices relative to the detected fiducial plane through each detected fiducial location and overlaying the detected fiducial locations on the one or more reconstructed oblique slices;

calculating a second registration error between the locations of the one or more fiducial markers on the one or more images and the detected fiducial locations on the one or more reconstructed oblique slices and determining whether the second registration error is equal to or above a threshold, wherein the one or more medical instruments or tools are to be inserted through an insertion point of a surface in a case where the registration error is equal to or above the threshold; and controlling a display to provide a visualization and a manipulation of the one or more registration results of the medical guidance device and/or guiding and controlling the one or more medical instruments or tools of the medical guidance device based on the second registration error.

* * * * *